United States Patent
Ootsuki et al.

(10) Patent No.: US 10,494,571 B2
(45) Date of Patent: Dec. 3, 2019

(54) POLYMERIZABLE LIQUID CRYSTAL COMPOUND, POLYMERIZABLE LIQUID CRYSTAL COMPOSITION, AND LIQUID CRYSTAL POLYMERIZED FILMS

(71) Applicants: JNC CORPORATION, Tokyo (JP); JNC PETROCHEMICAL CORPORATION, Tokyo (JP)

(72) Inventors: Daisuke Ootsuki, Chiba (JP); Nagahisa Miyagawa, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 84 days.

(21) Appl. No.: 15/795,272

(22) Filed: Oct. 27, 2017

(65) Prior Publication Data
US 2018/0119014 A1 May 3, 2018

(30) Foreign Application Priority Data
Oct. 28, 2016 (JP) .................... 2016-211212

(51) Int. Cl.
G02F 1/1333 (2006.01)
C09K 19/38 (2006.01)
G02F 1/1335 (2006.01)
G02B 5/30 (2006.01)
C07C 69/94 (2006.01)

(52) U.S. Cl.
CPC .......... C09K 19/3809 (2013.01); C07C 69/94 (2013.01); G02B 5/3016 (2013.01); G02F 1/133528 (2013.01)

(58) Field of Classification Search
CPC ............. G02F 1/1333; G02F 1/133528; G02B 5/3016; C07C 69/92; C07C 69/94; C07C 2601/14; C07C 2601/18; C09K 2019/0448; C09K 19/3809; C09K 19/2007; C09K 19/2014; C09K 19/32; C09K 19/322
USPC ...................................... 252/299.64
See application file for complete search history.

(56) References Cited

U.S. PATENT DOCUMENTS 9,080,100 B2 * 7/2015 Hirai .................. C09K 19/3809
9,399,736 B2 * 7/2016 Hirai ...................... C09K 19/56
9,505,980 B2 * 11/2016 Hirai ...................... C09K 19/32

FOREIGN PATENT DOCUMENTS

JP 2016051178 4/2016

\* cited by examiner

*Primary Examiner* — Geraldina Visconti
(74) *Attorney, Agent, or Firm* — JCIPRNET

(57) ABSTRACT

To provide a polymerizable liquid crystal compound in order to produce a retardation film having excellent front contrast. A polymerizable liquid crystal composition including a compound represented by Formula (1).

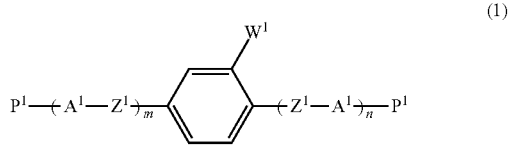

(1)

In Formula (1), for example, $W^1$ is an alkoxycarbonyl group having 1 to 10 carbon atoms, an alkanoyl group having 1 to 10 carbon atoms, or a polymerizable functional group, $A^1$ is independently 1,4-phenylene or naphthalene-2,6-diyl, $Z^1$ is a linking group, m and n are independently an integer of 0 to 7, and satisfy $3 \leq m+n \leq 8$, and $P^1$ is a polymerizable functional group.

14 Claims, No Drawings

POLYMERIZABLE LIQUID CRYSTAL COMPOUND, POLYMERIZABLE LIQUID CRYSTAL COMPOSITION, AND LIQUID CRYSTAL POLYMERIZED FILMS

CROSS-REFERENCE TO RELATED APPLICATIONS

This application claims the priority benefit of Japanese application serial no. 2016-211212, filed on Oct. 28, 2016. The entirety of the above-mentioned patent application is hereby incorporated by reference herein and made a part of this specification.

BACKGROUND OF THE INVENTION

Field of the Invention

The present invention relates to a polymerizable liquid crystal compound for obtaining a retardation film having high front contrast, a polymerizable liquid crystal composition, and a liquid crystal polymerized film.

Description of Related Art

A liquid crystal polymerized film prepared by polymerizing a polymerizable liquid crystal composition can be used as materials of a display device having a film or an element having an optically anisotropic film for a retardation film, an optical compensation film, a reflective film, a selective reflection film, an antireflection film, a viewing angle compensation film, a liquid crystal alignment film, a polarizing element, a circularly polarizing element, and an elliptically polarizing element.

For example, in a liquid crystal display device, a retardation film is used for high quality image display. The liquid crystal polymerized film can be used as a retardation film because it exhibits birefringence. In the related art, a stretched polymer film exhibiting birefringence has been used as a retardation film. For ease of film formation, thinning the film thickness, and improvement in durability, a retardation film using a liquid crystal polymerized film has been studied.

A display device having high contrast can display so that colors close in brightness can be distinguished. Therefore, a display device including a retardation film having high front contrast therein is required for high quality image display. There is an example in which front contrast of a retardation film is improved according to a liquid crystal polymerized film fixed in a smectic phase (Patent Document 1).

PRIOR ART DOCUMENTS

Patent Documents

[Patent Document 1] Japanese Unexamined Patent Application Publication No. 2016-051178

SUMMARY OF THE INVENTION

The present invention provides a retardation film having high front contrast. The present invention further provides a polymerizable liquid crystal compound for preparing a retardation film having high front contrast, and a polymerizable liquid crystal composition and liquid crystal polymerized film including the polymerizable liquid crystal compound.

The inventors found that a liquid crystal polymerized film prepared using a polymerizable liquid crystal composition containing a specific polymerizable liquid crystal compound can provide a retardation film having high front contrast, and completed the invention.

[1] A polymerizable liquid crystal composition containing a compound represented by Formula (1),

[Chem. 1]

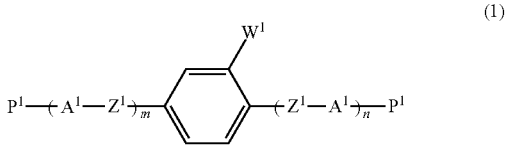

(1)

in Formula (1), $W^1$ is alkoxycarbonyl group having 1 to 10 carbon atoms, an alkanoyl group having 1 to 10 carbon atoms or a group represented by Formula (2), and at least one —$CH_2$— in the alkoxycarbonyl may be optionally replaced with —O—, $A^1$ is independently 1,4-phenylene or naphthalene-2,6-diyl, and at least one hydrogen of 1,4-phenylene and naphthalene-2,6-diyl may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms, $Z^1$ is independently —$CH_2CH_2$—, —COO—, —OCO—, —$CH_2O$—, —$OCH_2$—, —$OCH_2CH_2O$—, —CH=CHCOO—, —OCOCH=CH—, —$CH_2CH_2COO$—, —$OCOCH_2CH_2$—, —$CH_2CH_2OCO$—, or —$COOCH_2CH_2$—, m and n are independently an integer of 0 to 7, and satisfy 3≤m+n≤8, and $P^1$ is independently a group represented by Formula (2).

[Chem. 2]

(2)

In Formula (2), $Y^1$ is a single bond, —O—, —COO—, —OCO—, or —OCOO—, $Q^1$ is a single bond or an alkylene group having 1 to 20 carbon atoms, and at least one —$CH_2$— in the alkylene may be replaced with —O—, —COO—, or —OCO—, and PG is a functional group represented by any one of Formula (PG-1) to Formula (PG-9).

[Chem. 3]

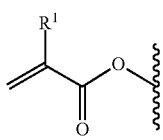

(PG-1)

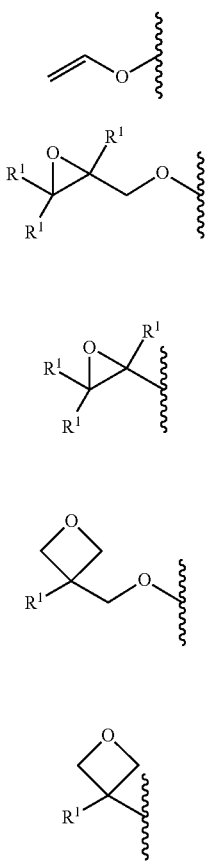

In Formula (PG-1) to Formula (PG-9), $R^1$ is independently hydrogen, a halogen, methyl, ethyl, or trifluoromethyl.

[2] The polymerizable liquid crystal composition according to [1], wherein m and n are independently 2 or 3.

[3] The polymerizable liquid crystal composition according to [1] or [2], wherein, in Formula (2), PG is a functional group represented by Formula (PG-1).

[4] The polymerizable liquid crystal composition according to any one of [1] to [3], wherein $Z^1$ is independently —COO—, —OCO—, —CH$_2$CH$_2$COO—, or —OCOCH$_2$CH$_2$—, and at least one of $Z^1$ is —CH$_2$CH$_2$COO— or —OCOCH$_2$CH$_2$—.

[5] The polymerizable liquid crystal composition according to any one of [1] to [4], wherein the compound represented by Formula (1) is contained in an amount of 1 to 50% by weight based on a total weight of the polymerizable liquid crystal composition.

[6] The polymerizable liquid crystal composition according to any one of [1] to [5] further containing a compound represented by Formula (M1).

[Chem. 4]

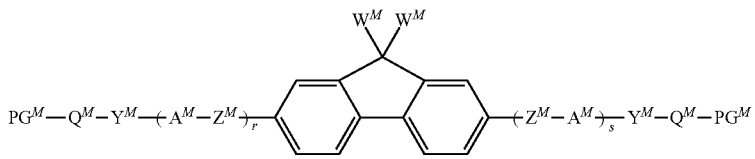

(In Formula (M1), $A^M$ is independently 1,4-phenylene, 1,4-cyclohexylene, or naphthalene-2,6-diyl, and at least one hydrogen in 1,4-phenylene or naphthalene-2,6-diyl may be replaced with fluorine, chlorine, cyano, formyl, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$ is independently a single bond, —CH$_2$CH$_2$—, —COO—, —OCO—, —C≡C—, —CH=CHCOO—, —OCOCH=CH—, —CH$_2$CH$_2$COO—, —OCOCH$_2$CH$_2$—, —CH$_2$CH$_2$OCO— or —COOCH$_2$CH$_2$—, r and s are independently an integer of 1 to 3, $W^M$ is independently hydrogen, fluorine, chlorine, an alkyl group having 1 to 10 carbon atoms, an alkenyl group having 2 to 10 carbon atoms, or a fluoroalkyl group having 1 to 10 carbon atoms, $Y^M$ is independently a single bond, —O—, —COO—, —OCO—, or —OCOO—, $Q^M$ is independently a single bond or an alkylene group having 1 to 20 carbon atoms, and at least one —CH$_2$— in the alkylene may be replaced with —O—, —COO—, or —OCO—, and $PG^M$ is independently a functional group represented by any one of Formula (PG-1) to Formula (PG-9).

[Chem. 5]

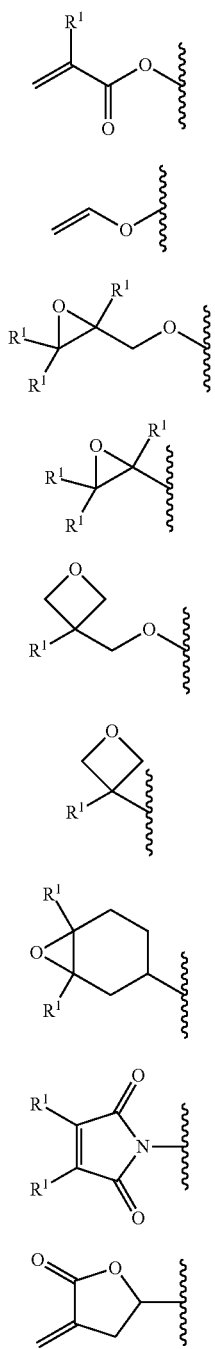

(PG-1)
(PG-2)
(PG-3)
(PG-4)
(PG-5)
(PG-6)
(PG-7)
(PG-8)
(PG-9)

(In Formula (PG-1) to Formula (PG-9), $R^1$ is independently hydrogen, a halogen, methyl, ethyl, or trifluoromethyl.)

[7] The polymerizable liquid crystal composition according to [6], wherein the compound represented by Formula (1) is contained in an amount of 10 to 90% by weight based on a total weight of the compound represented by Formula (1) and the compound represented by Formula (M1).

[8] The polymerizable liquid crystal composition according to [6], wherein, in Formula (M1), $PG^M$ is a functional group represented by Formula (PG-1).

[9] A liquid crystal polymerized film obtained by polymerizing the polymerizable liquid crystal composition according to any one of [1] to [7].

[10] The liquid crystal polymerized film according to [9], wherein liquid crystal molecules are fixed in a state where the liquid crystal molecules are aligned by the photoalignment film.

[11] A retardation film composed of the liquid crystal polymerized film according to [9] or [10].

[12] A polarizing plate having the liquid crystal polymerized film according to [9] or [10].

[13] A display device having the liquid crystal polymerized film according to [9] or [10].

[14] A polymerizable liquid crystal compound represented by Formula (1-1).

[Chem. 6]

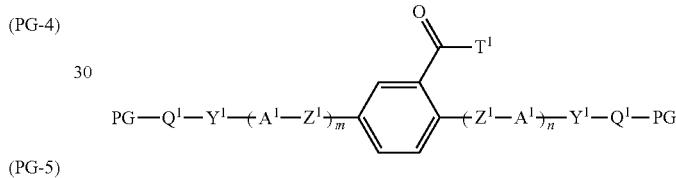

(1-1)

In Formula (1-1), $T^1$ is an alkyl group having 1 to 10 carbon atoms or an alkoxy group having 1 to 10 carbon atoms, $A^1$ is independently 1,4-phenylene, and at least one hydrogen in 1,4-phenylene may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms, $Z^1$ is independently —COO—, —OCO—, —CH$_2$CH$_2$COO—, or —OCOCH$_2$CH$_2$—, m and n each are 2 or 3, $Y^1$ is a single bond, —O—, —COO—, —OCO—, or —OCOO—, $Q^1$ is a single bond or an alkylene group having 1 to 20 carbon atoms, and at least one —CH$_2$— in the alkylene may be replaced with —O—, —COO—, or —OCO—, and PG is a functional group represented by any one of Formula (PG-1) to Formula (PG-9).

[Chem. 7]

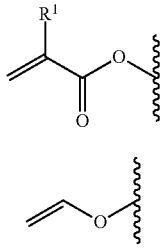

(PG-1)

(PG-2)

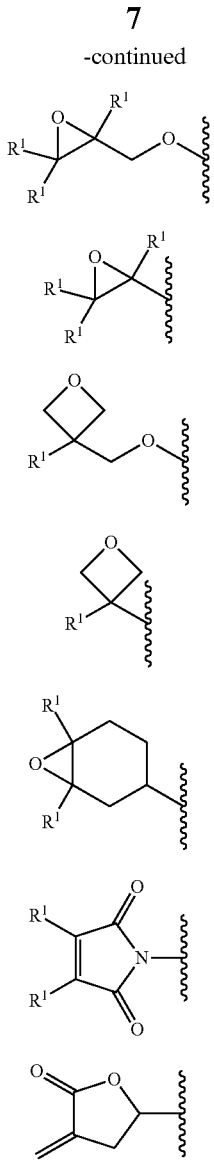

In Formula (PG-1) to Formula (PG-9), $R^1$ is independently hydrogen, a halogen, methyl, ethyl, or trifluoromethyl.

DESCRIPTION OF THE EMBODIMENTS

When a polymerizable liquid crystal compound which has a phenylene skeleton including a substituent at a lateral position and in which five or more ring structures of a single ring and a condensed ring are combined and are linked as shown in Formula (1) is added to a polymerizable liquid crystal composition, which is a raw material of a liquid crystal polymerized film, it is possible to produce a liquid crystal polymerized film having high front contrast.

In the present invention, "front contrast" means a value of (luminance in a parallel nicols state)/(luminance in a crossed nicols state) when a liquid crystal polymerized film with a substrate is disposed between two polarizing plates.

In the present invention, a "crossed nicols state" refers to a state in which polarization axes of polarizing plates disposed to face each other are orthogonal.

In the present invention, a "parallel nicols state" refers to a state in which polarization axes of polarizing plates disposed to face each other are aligned.

In the present invention, a "compound (X)" means a compound represented by Formula (X). Here, X in the "compound (X)" is a string, a number, a symbol, or the like.

In the present invention, a "liquid crystal composition" is a mixture having a liquid crystal phase.

In the present invention, a "liquid crystal compound" is a general term of (A) a compound having a liquid crystal phase as a pure substance and (B) a compound which is a component of a liquid crystal composition.

In the present invention, a "polymerizable functional group" is a functional group of which polymerization occurs according to a method using light, heat, or a catalyst, and change to a polymer having a higher molecular weight occurs when it is included in a compound.

In the present invention, a "monofunctional compound" is a compound including one polymerizable functional group.

In the present invention, a "multi-functional compound" is a compound including a plurality of polymerizable functional groups.

In the present invention, an "X-functional compound" is a compound including X polymerizable functional groups. Here, X in the "X-functional compound" is an integer.

In the present invention, a "polymerizable compound" is a compound including at least one polymerizable functional group.

In the present invention, a "polymerizable liquid crystal compound" is a polymerizable compound which is a liquid crystal compound.

In the present invention, a "non-liquid crystalline polymerizable compound" is a polymerizable compound which is a compound having no liquid crystal phase in a pure substance.

In the present invention, a "polymerizable liquid crystal composition" means a composition including a polymerizable compound and a liquid crystal compound or a composition including a "polymerizable liquid crystal compound."

In the present invention, a "liquid crystal polymerized film" means a product obtained by polymerizing a polymerizable liquid crystal composition.

In the present invention, a "liquid crystal polymerized film with a substrate" means a product that is obtained by polymerizing a polymerizable liquid crystal composition on a substrate and includes a substrate.

In the present invention, a "liquid crystal polymerized film" is a general term of a liquid crystal polymerized film and a liquid crystal polymerized film with a substrate.

In the present invention, a "retardation film" is a polarization conversion element having optical anisotropy and is a product that is mainly used for an optical element.

In the present invention, a "tilt angle" is an angle between an alignment direction of long axes of liquid crystal molecules and a surface of a substrate.

In the present invention, "homogeneous alignment" refers to an alignment state in which a tilt angle is 0 degrees to 5 degrees.

In the present invention, "homeotropic alignment" refers to an alignment state in which a tilt angle is 85 degrees to 90 degrees.

In the present invention, "tilt alignment" refers to an alignment state in which an alignment direction of long axes of liquid crystal molecules rises from parallel to a substrate to perpendicular thereto, moving away from the substrate.

In the present invention, "twist alignment" refers to an alignment state in which an alignment direction of liquid crystal molecules in the long axis direction is parallel to a substrate, and when liquid crystal molecules move away from the substrate, twisting occurs stepwise using a line perpendicular to a surface of the substrate as an axis.

In the present invention, "room temperature" refers to a temperature range of 15° C. to 35° C.

When the following functional group is shown in a chemical formula, this means that a wavy line part is a binding position of the functional group. Here, the following C is an arbitrary atom or functional part.

[Chem. 8]

<Polymerizable Liquid Crystal Compound>

A polymerizable liquid crystal composition containing a compound (1) can be used to produce a liquid crystal polymerized film having high front contrast. The liquid crystal polymerized film is a material of a retardation film.

A display device including a retardation film having high front contrast is required since it can display a wide range of color tone. A polarizing plate is a type of optical element. A polarizing plate having high front contrast is required.

In a polymerizable liquid crystal composition containing the compound (1) of the present invention which contains a large amount of a polymerizable liquid crystal compound, even after a solvent is removed, no crystals will precipitate from the polymerizable liquid crystal composition. In addition, when the polymerizable liquid crystal composition is used as a raw material, it is possible to obtain a liquid crystal polymerized film without an alignment defect.

[Chem. 9]

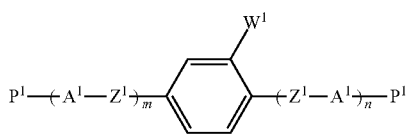

(1)

In Formula (1), $W^1$ is an alkoxycarbonyl group having 1 to 10 carbon atoms, an alkanoyl group having 1 to 10 carbon atoms or is a group represented by Formula (2), and at least one —$CH_2$— in the alkoxycarbonyl may be replaced with —O—.

[Chem. 10]

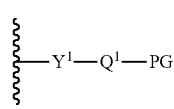

(2)

In Formula (2), $Y^1$ is a single bond, —O—, —COO—, —OCO—, or —OCOO—, $Q^1$ is a single bond or an alkylene group having 1 to 20 carbon atoms, at least one —$CH_2$— in the alkylene may be replaced with —O—, —COO—, or —OCO—, and PG is a functional group represented by any one of Formula (PG-1) to Formula (PG-9).

[Chem. 11]

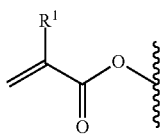

(PG-1)

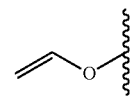

(PG-2)

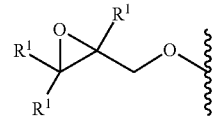

(PG-3)

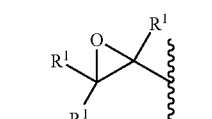

(PG-4)

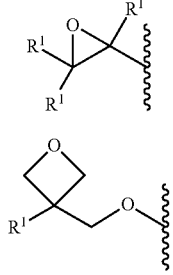

(PG-5)

(PG-6)

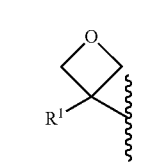

(PG-7)

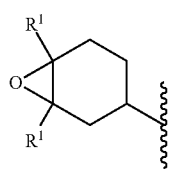

(PG-8)

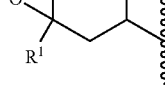

(PG-9)

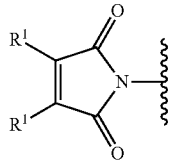

(In Formula (PG-1) to Formula (PG-9), $R^1$ is independently hydrogen, a halogen, methyl, ethyl, or trifluoromethyl.)

When $W^1$ is an alkoxycarbonyl group having 1 to 10 carbon atoms, phase separation with respect to other liquid crystalline compounds in the polymerizable liquid crystal composition and an organic solvent becomes difficult. When $W^1$ is an alkanoyl group having 1 to 10 carbon atoms, a temperature range of a liquid crystal phase of the polymerizable liquid crystal composition becomes wider and birefringence increases. When $W^1$ is a group represented by Formula (2), a mechanical strength of a liquid crystal polymerized film obtained using the polymerizable liquid crystal composition increases.

$A^1$ is independently 1,4-phenylene or naphthalene-2,6-diyl, and in these rings, at least one hydrogen may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms.

$Z^1$ is independently —CH$_2$CH$_2$—, —COO—, —OCO—, —CH$_2$O—, —OCH$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, or —COOCH$_2$CH$_2$—. $Z^1$ is independently —COO—, —OCO—, —CH$_2$CH$_2$COO—, or —OCOCH$_2$CH$_2$—, and when at least one of $Z^1$ is —CH$_2$CH$_2$COO— or —OCOCH$_2$CH$_2$—, this is more preferable because a liquid crystal temperature range of the polymerizable liquid crystal composition becomes broader, and phase separation with respect to other liquid crystalline compounds in the polymerizable liquid crystal composition and an organic solvent becomes difficult.

m and n are independently an integer of 0 to 7, and satisfy 3≤m+n≤8. In order to increase front contrast, m+n≥3 is preferable. In order to prevent phase separation with respect to other liquid crystalline compounds in the polymerizable liquid crystal composition and an organic solvent, m+n≤8 is preferable, and m and n are more preferably 2 or 3.

$P^1$ is independently a group represented by Formula (2).

[Chem. 12]

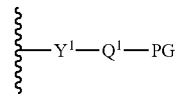

(2)

(in Formula (2), $Y^1$ is a single bond, —O—, —COO—, —OCO—, or —OCOO—, $Q^1$ is a single bond or an alkylene group having 1 to 20 carbon atoms, at least one —CH$_2$— in the alkylene may be replaced with —O—, —COO—, or —OCO—, and PG is a functional group represented by any one of Formula (PG-1) to Formula (PG-9).

[Chem. 13]

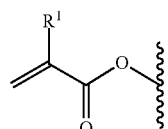
(PG-1)

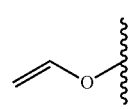
(PG-2)

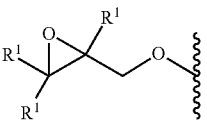
(PG-3)

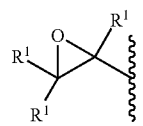
(PG-4)

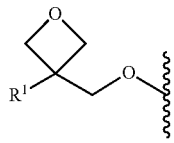
(PG-5)

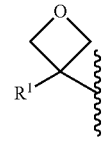
(PG-6)

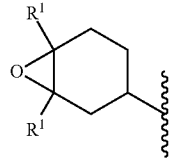
(PG-7)

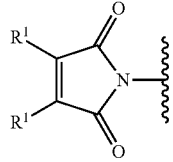
(PG-8)

(PG-9)

(In Formula (PG-1) to Formula (PG-9), $R^1$ is independently hydrogen, a halogen, methyl, ethyl, or trifluoromethyl.)

In Formula (2), when $Q^1$ is an alkylene group having 1 to 20 carbon atoms, a liquid crystal phase of the polymerizable liquid crystal composition is easily induced, and phase separation with respect to other liquid crystalline compounds and an organic solvent becomes difficult.

PG is independently a functional group represented by any one of Formula (PG-1) to Formula (PG-9).

Functional groups represented by Formula (PG-1), Formula (PG-8), and Formula (PG-9) are polymerizable functional groups of which polymerization occurs according to various methods and change to a polymer having a higher molecular weight occurs because they have an α,β unsaturated ketone structure.

Formula (PG-2) is a polymerizable functional group of which polymerization occurs according to various methods and change to a polymer having a higher molecular weight occurs because it has a vinyl group adjacent to an electron donating group.

Functional groups represented by Formula (PG-3) to Formula (PG-7) are polymerizable functional groups of which polymerization occurs according to various methods and change to a polymer having a higher molecular weight occurs because they have a strained cyclic ether.

Functional groups represented by Formula (PG-1) to Formula (PG-9) can be appropriately selected according to film production conditions. For example, when a film is produced according to light curing that is generally used, in consideration of high curability, solubility in a solvent, and ease of handling, an acrylic group or methacrylic group represented by Formula (PG-1) is preferable.

Among polymerizable liquid crystal compounds represented by Formula (1), in consideration of compatibility with other liquid crystalline compounds and an organic solvent, a compound represented by Formula (1-1) is preferable, and compounds represented by Formula (1-1-1) to Formula (1-1-10) and Formula (1-2-1) to Formula (1-2-5) are more preferable.

A polymerizable liquid crystal compound represented by Formula (1-1), (1-1)

$$PG-Q^1-Y^1-(A^1-Z^1)_m-\phantom{X}-(Z^1-A^1)_n-Y^1-Q^1-PG$$

(in Formula (1-1), $T^1$ is an alkyl group having 1 to 10 carbon atoms or an alkoxy group having 1 to 10 carbon atoms, $A^1$ is independently 1,4-phenylene, and at least one hydrogen in 1,4-phenylene may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms, $Z^1$ is independently —COO—, —OCO—, —CH$_2$CH$_2$COO—, or —OCOCH$_2$CH$_2$—, m and n each are 2 or 3, $Y^1$ is a single bond, —O—, —COO—, —OCO—, or —OCOO—, $Q^1$ is a single bond or an alkylene group having 1 to 20 carbon atoms, and at least one —CH$_2$— in the alkylene may be replaced with —O—, —COO—, or —OCO—, and PG is a functional group represented by any one of Formula (PG-1) to Formula (PG-9).

[Chem. 14]

(PG-1)

(PG-2)

(PG-3)

(PG-4)

(PG-5)

(PG-6)

(PG-7)

(PG-8)

(PG-9)

(In Formula (PG-1) to Formula (PG-9), $R^1$ is independently hydrogen, a halogen, methyl, ethyl, or trifluoromethyl.)

[Chem. 15]

(1-1-1)

$$PG-Q^1-Y^1-\phantom{X}-Y^1-Q^1-PG$$

-continued
(1-1-2)
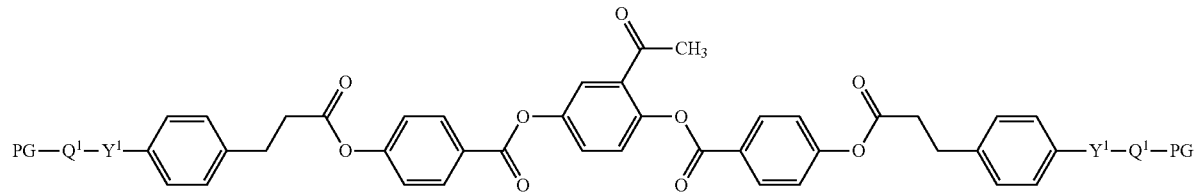
(1-1-3)
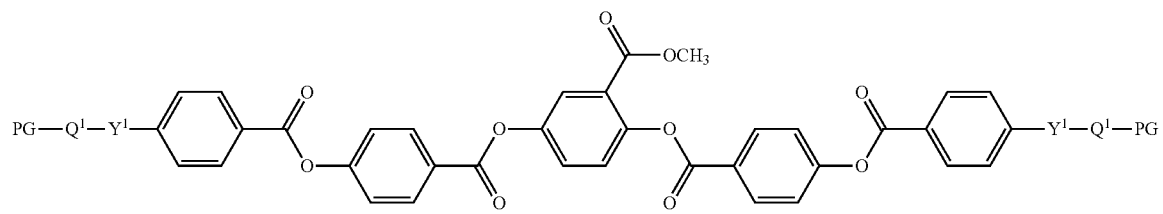
(1-1-4)
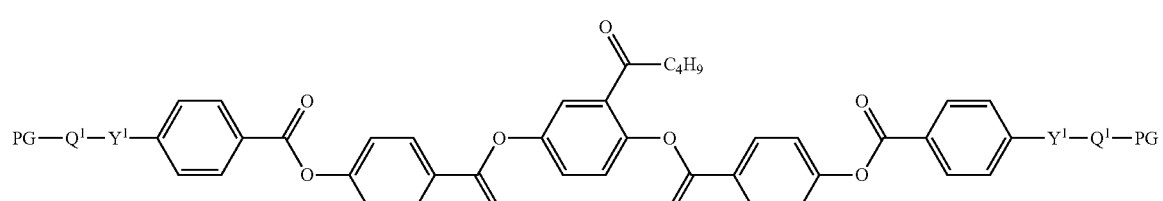
(1-1-5)
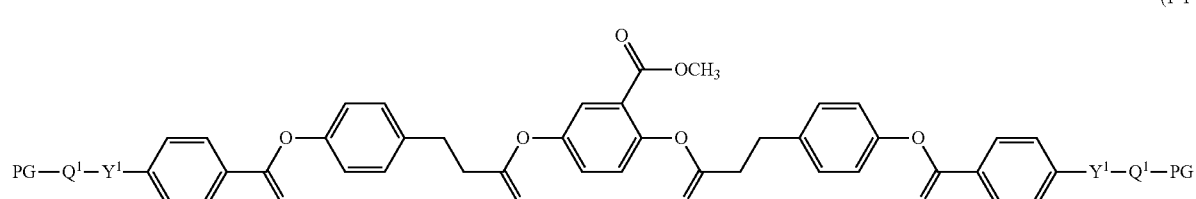
(1-1-6)
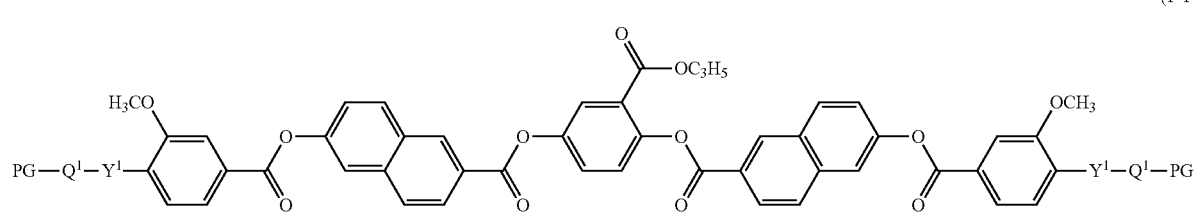
(1-1-7)
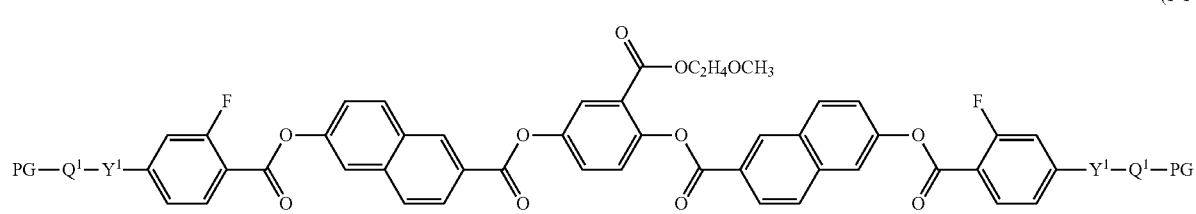
(1-1-8)
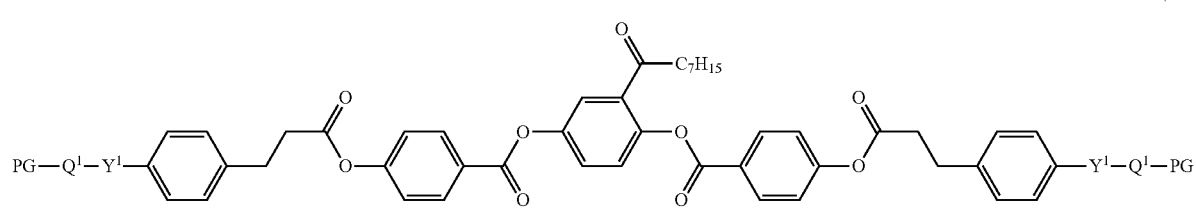

[Chem. 16]
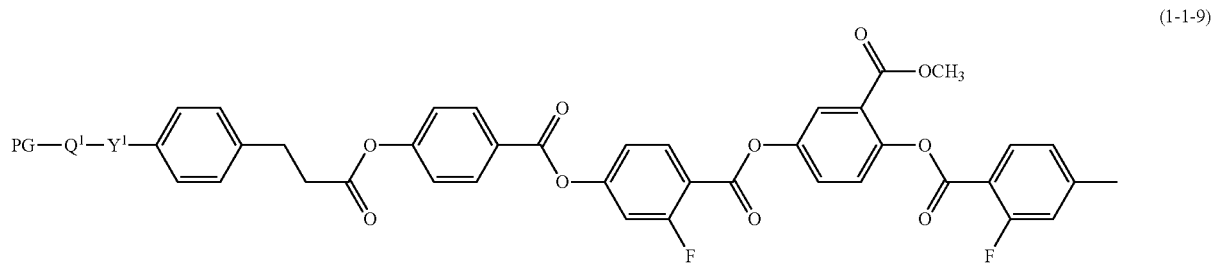
(1-1-9)
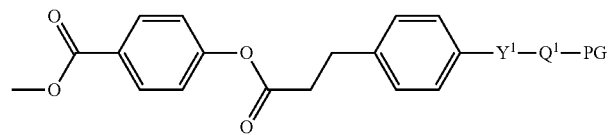
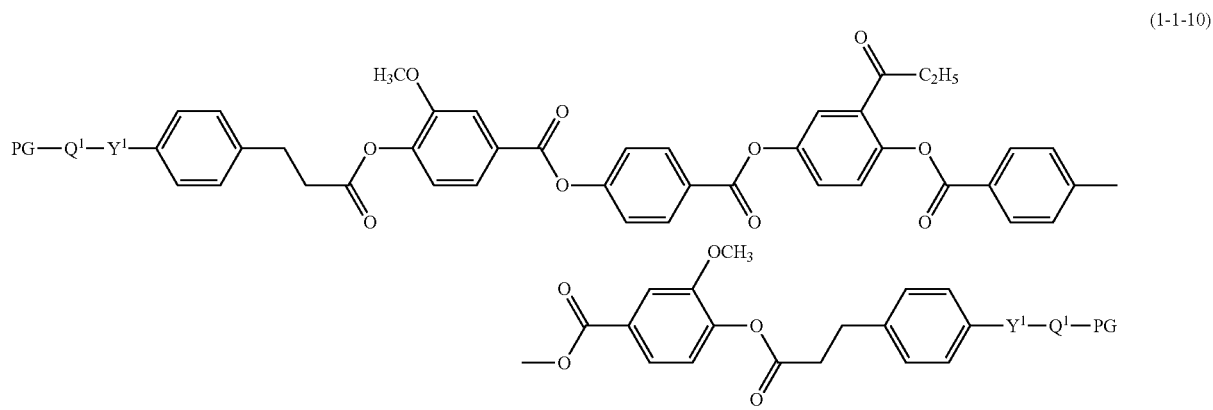
(1-1-10)
[Chem. 17]
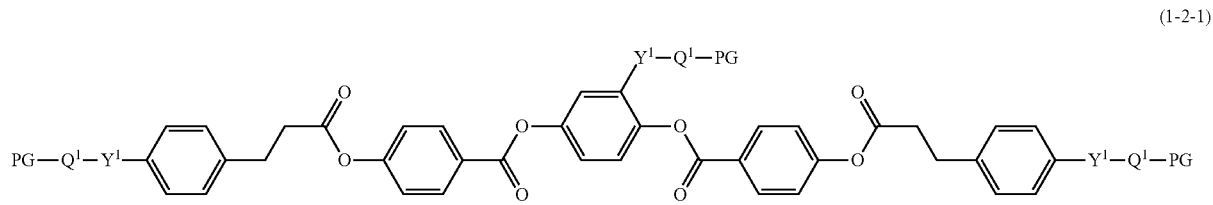
(1-2-1)
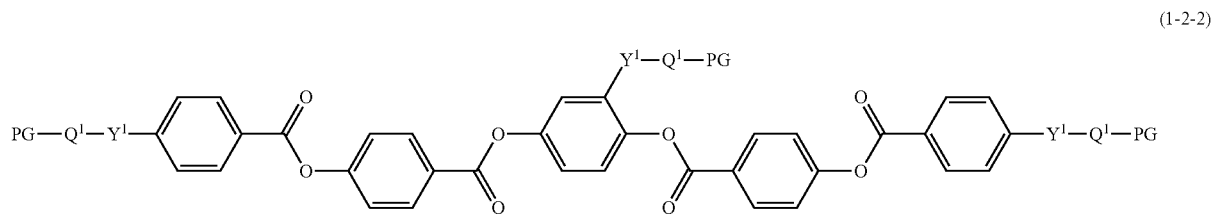
(1-2-2)

(1-2-3)

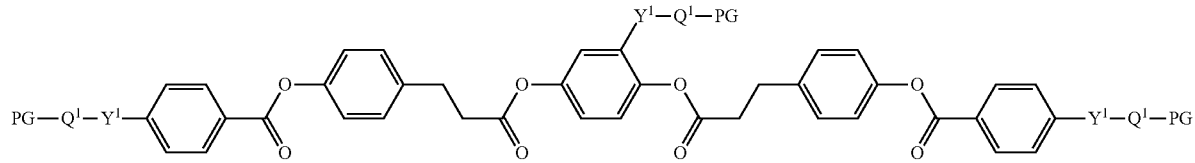

(1-2-4)

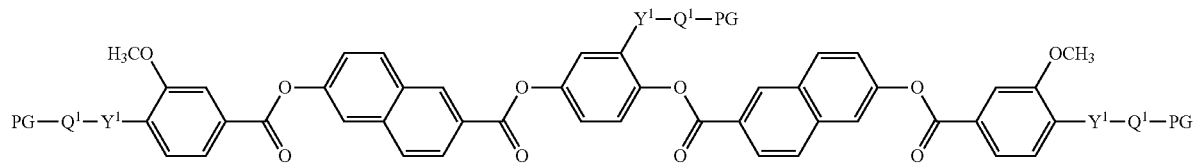

(1-2-5)

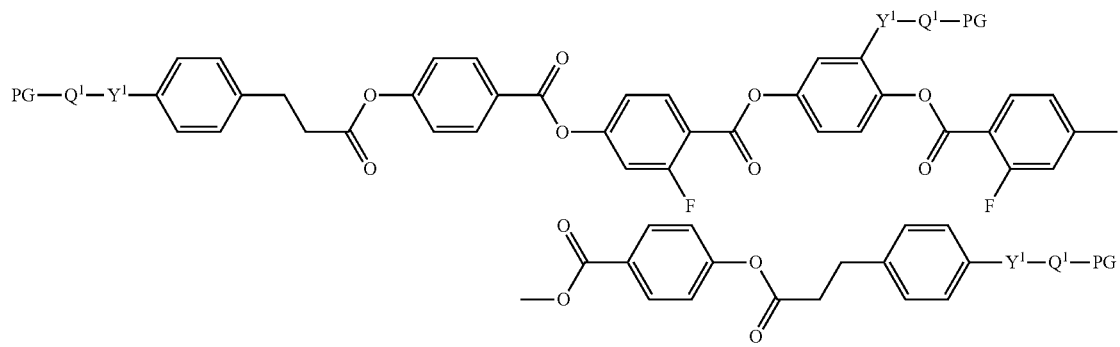

In Formula (1-1-1) to Formula (1-1-10) or Formula (1-2-1) to Formula (1-2-5), $Y^1$ is independently a single bond, —O—, —COO—, —OCO—, or —OCOO—, $Q^1$ is independently a single bond or an alkylene group having 1 to 20 carbon atoms, at least one —CH$_2$— in the alkylene may be replaced with —O—, —COO—, or —OCO—, and PG is independently any one of functional groups represented by Formula (PG-1) to Formula (PG-9).

The compound (1) can be synthesized by combining known organic synthetic chemistry methods. For example, as a starting material, a material synthesized in the same manner as in ACS. Medicinal. Chemistry. Letters. 2010. 1 (7). 345-349 may be used and synthesis can be performed according to a reaction scheme shown in the following Example 1.

<Polymerizable Liquid Crystal Composition>

A polymerizable liquid crystal composition of the present invention contains one or more compounds (1). In order to improve front contrast, in the polymerizable liquid crystal composition of the present invention, with respect to a total amount of the polymerizable liquid crystal composition, preferably, 1 to 50% by weight of the compound (1) is contained and more preferably 3 to 30% by weight of the compound (1) is contained.

The polymerizable liquid crystal composition of the present invention may contain a polymerizable liquid crystal compound other than the polymerizable liquid crystal compound represented by the compound (1). In consideration of inducing a liquid crystal phase from the polymerizable liquid crystal composition and compatibility with the compound (1) and an organic solvent, a compound represented by the following Formula (M1) is preferable as the polymerizable liquid crystal compound.

[Chem. 18]

(M1)

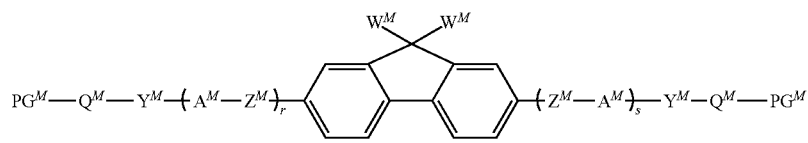

In Formula (M1), $A^M$ is independently 1,4-phenylene, 1,4-cyclohexylene, or naphthalene-2,6-diyl, and at least one hydrogen in 1,4-phenylene or naphthalene-2,6-diyl may be replaced with fluorine, chlorine, cyano, formyl, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$ is independently a single bond, —CH$_2$CH$_2$—, —COO—, —OCO—, —C≡C—, —CH═CHCOO—, —OCOCH═CH—, —CH$_2$CH$_2$COO—, —OCOCH$_2$CH$_2$—, —CH$_2$CH$_2$OCO— or —COOCH$_2$CH$_2$—, r and s are independently an integer of 1 to 3, $W^M$ is independently hydrogen, fluorine, chlorine, an alkyl group having 1 to 10 carbon atoms, an alkenyl group having 2 to 10 carbon atoms, or a fluoroalkyl group having 1 to 10 carbon atoms, $Y^M$ is independently a single bond, —O—, —COO—, —OCO—, or —OCOO—, $Q^M$ is independently a single bond or an alkylene group having 1 to 20 carbon atoms, and at least one —CH$_2$— in the alkylene may be replaced with —O—, —COO—, or —OCO—, and $PG^M$ is independently a functional group represented by any one of Formula (PG-1) to Formula (PG-9).

[Chem. 19]

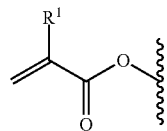

(PG-1)

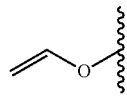

(PG-2)

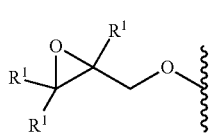

(PG-3)

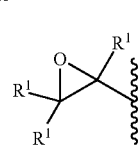

(PG-4)

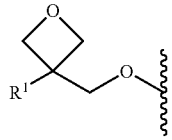

(PG-5)

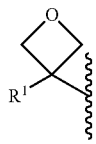

(PG-6)

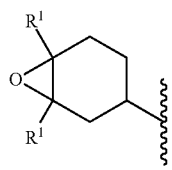

(PG-7)

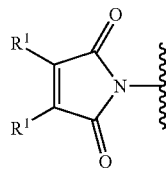

(PG-8)

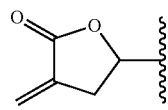

(PG-9)

(In Formula (PG-1) to Formula (PG-9), $R^1$ is independently hydrogen, a halogen, methyl, ethyl, or trifluoromethyl.

In consideration of improvement in front contrast of the liquid crystal polymerized film, inducing a liquid crystal phase from the polymerizable liquid crystal composition which is a raw material of the liquid crystal polymerized film, and prevention of phase separation with respect to other liquid crystalline compounds in the component and an organic solvent, a total amount of the compound represented by Formula (M1) in the polymerizable liquid crystal composition is preferably 10 to 90% by weight and more preferably 10 to 70% by weight based on a total weight of the compounds represented by Formula (1) and Formula (M1).

Formula (M1-1) to Formula (M1-6) are compounds represented by Formula (M1).

[Chem. 20]

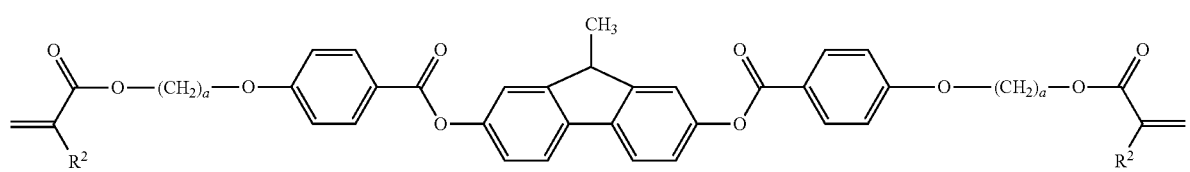

(M1-1)

(M1-2)
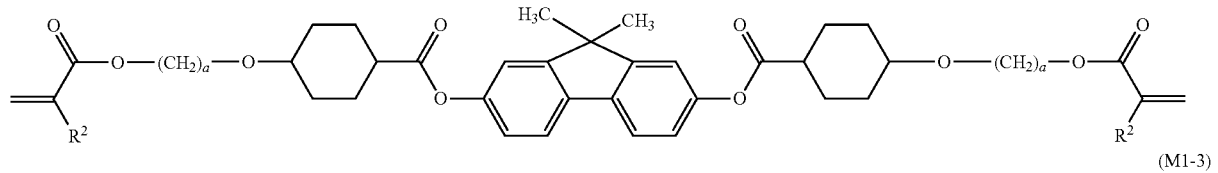
(M1-3)
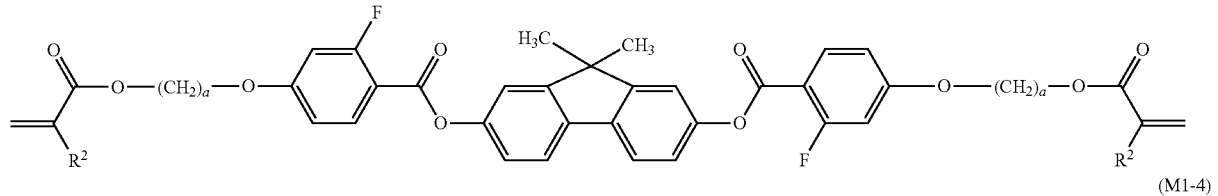
(M1-4)
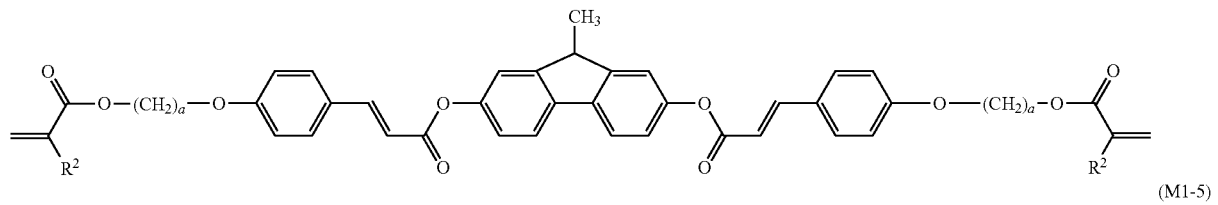
(M1-5)
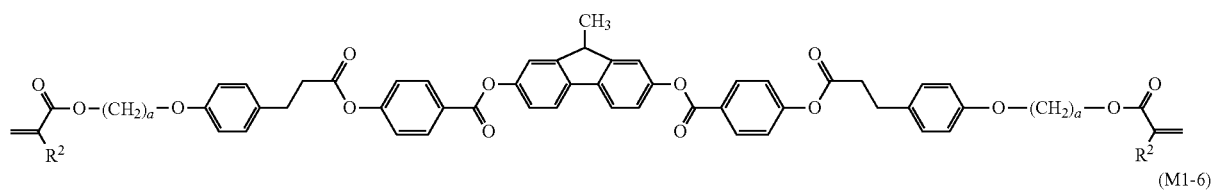
(M1-6)
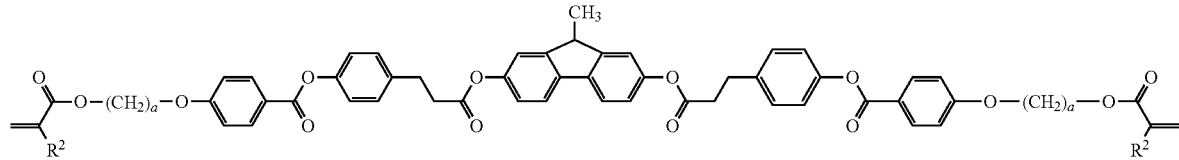
In Formula (M1-1) to Formula (M1-6), $R^2$ is independently hydrogen or methyl, and a is independently an integer of 1 to 12.
The polymerizable liquid crystal composition of the present invention may contain a polymerizable liquid crystal compound (M2) other than the compound (1) and the compound (M1). Compounds represented by Formula (M2-1) to Formula (M2-8) are compounds (M2).
[Chem. 21]
(M2-1)
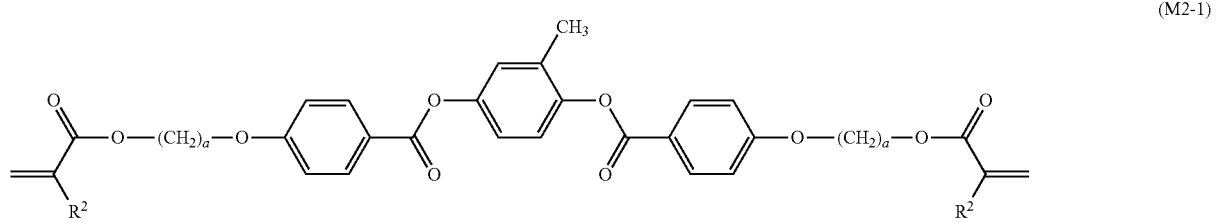
(M2-2)
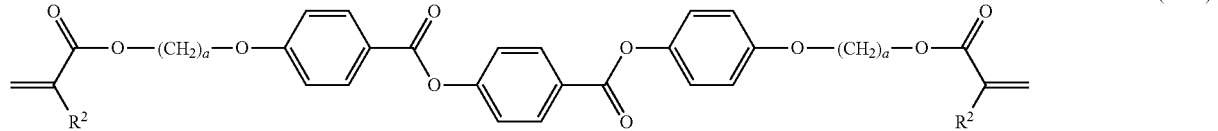

-continued

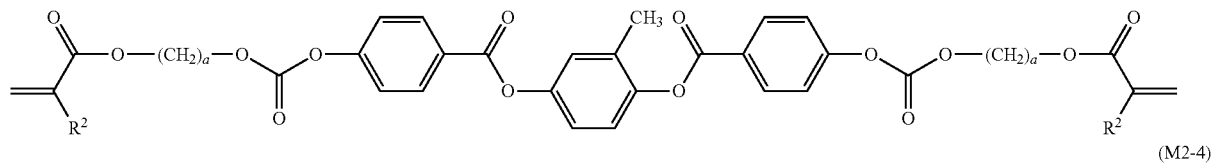
(M2-3)

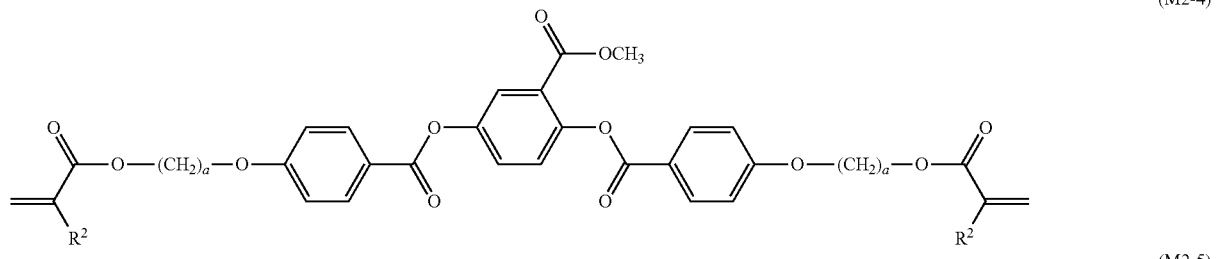
(M2-4)

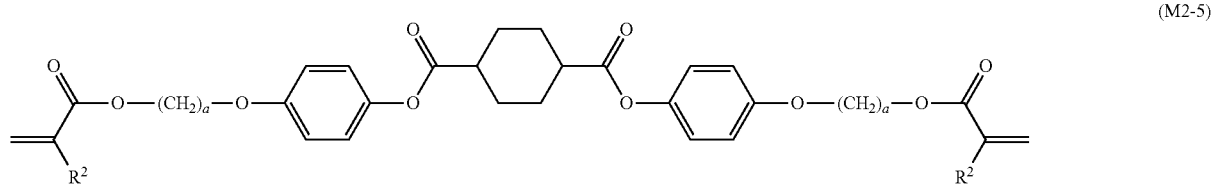
(M2-5)

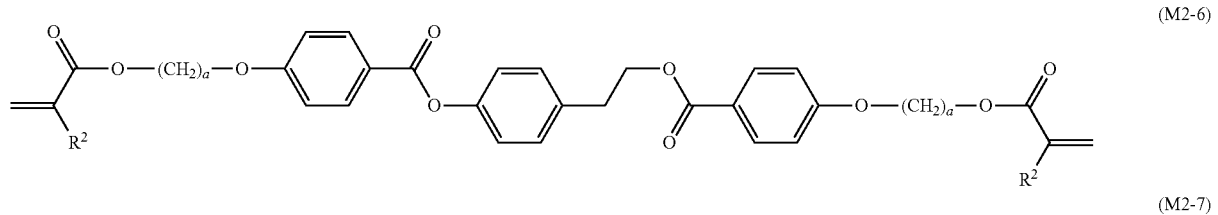
(M2-6)

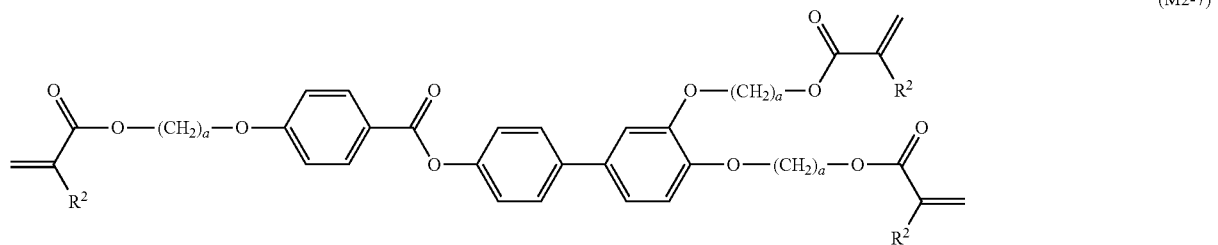
(M2-7)

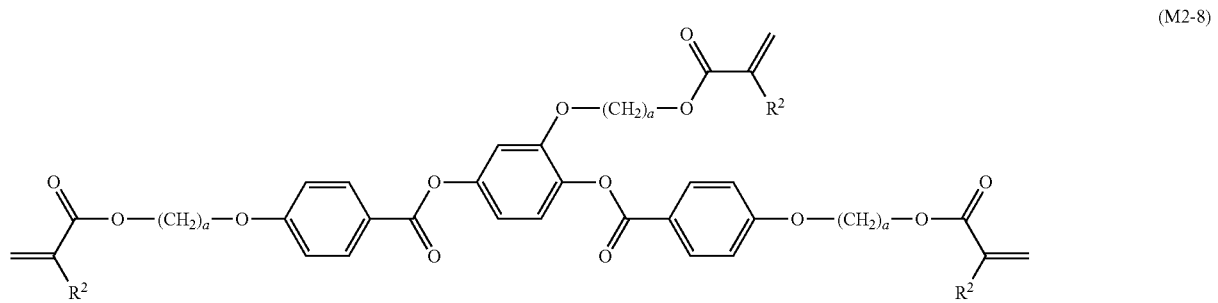
(M2-8)

In Formula (M2-1) to Formula (M2-8), $R^2$ is independently hydrogen or methyl, and a is independently an integer of 1 to 12.

The polymerizable liquid crystal composition of the present invention is applied onto a plastic substrate to which an alignment treatment such as a rubbing treatment is performed or a support substrate whose surface is covered with a thin plastic film to form a film, and thus a homogeneously aligned or tilt-aligned liquid crystal polymerized film is obtained.

<Additives for Polymerizable Liquid Crystal Composition>

Additives of one or more types may be added to the polymerizable liquid crystal composition of the present invention.

When a surfactant is added to the polymerizable liquid crystal composition, smoothness of the liquid crystal polymerized film is improved. When a nonionic surfactant is added to the polymerizable liquid crystal composition, smoothness of the liquid crystal polymerized film is further improved. The nonionic surfactant has an effect of preventing tilt alignment on the side of an air interface of the liquid crystal polymerized film. A silicone-based nonionic surfactant, a fluorine-based nonionic surfactant, a vinyl-based nonionic surfactant, and a hydrocarbon-based nonionic surfactant may be the nonionic surfactant.

In order to improve a mechanical strength and chemical resistance of the surface of the liquid crystal polymerized film, a surfactant which is a polymerizable compound is preferably added to the polymerizable liquid crystal composition, and a surfactant that initiates a polymerization reaction with ultraviolet light is more preferable.

In order for the liquid crystal polymerized film to be likely to be uniformly aligned and in order to improve a coating property of the polymerizable liquid crystal composition, there is preferably 0.0001 to 0.5% by weight and more preferably 0.01 to 0.2% by weight of a surfactant in the polymerizable liquid crystal composition with respect to a total amount of the polymerizable liquid crystal composition.

Surfactants are classified into ionic surfactants and nonionic surfactants.

A silicone-based nonionic surfactant, a fluorine-based nonionic surfactant, and a vinyl-based nonionic surfactant are nonionic surfactants.

Titanate compounds, imidazoline, quaternary ammonium salts, alkylamine oxides, polyamine derivatives, polyoxyethylene-polyoxypropylene condensates, polyethylene glycols, and esters thereof, sodium lauryl sulfate, ammonium lauryl sulfate, amine lauryl sulfates, alkyl substituted aromatic sulfonates, alkyl phosphates, aliphatic or aromatic sulfonic acid formalin condensates, lauryl amidopropyl betaines, lauryl amino acetic acid betaines, polyethylene glycol fatty acid esters, polyoxyethylene alkyl amines, perfluoroalkyl sulfonates, and perfluoroalkyl carboxylates may be the ionic surfactant.

A compound which is a linear polymer including a siloxane bond and has a side chain and/or terminal to which an organic group such as a polyether and a long chain alkyl is introduced is a silicone-based nonionic surfactant.

A compound having a perfluoroalkyl group or perfluoroalkenyl group having 2 to 7 carbon atoms is a fluorine-based nonionic surfactant.

As the vinyl-based nonionic surfactant, a (meth)acrylic polymer with a weight average molecular weight of 1,000 to 1,000,000 may be exemplified.

When a surfactant having a polymerizable functional group is added to the polymerizable liquid crystal composition which is a raw material of the liquid crystal polymer film, hardness of the surface of the liquid crystal polymerized film is improved.

The polymerizable liquid crystal composition of the present invention may contain a non-liquid crystalline polymerizable compound. In order to maintain a liquid crystal phase, a total weight of the non-liquid crystalline polymerizable compound in the polymerizable liquid crystal composition is preferably one fifth or less of a total weight of the polymerizable compounds in the polymerizable liquid crystal composition.

When a compound having two or more polymerizable functional groups is added to the polymerizable liquid crystal composition, either or both of improvement in mechanical strength of the liquid crystal polymerized film and improvement in chemical resistance can be expected.

The non-liquid crystalline polymerizable compound is typically a compound having one or two or more vinyl-based polymerizable functional groups When a non-liquid crystalline polymerizable compound having a polar group in a side chain and/or terminal is added to the polymerizable liquid crystal composition, improvement in adhesiveness between the polymerizable liquid crystal composition and a substrate can be expected.

Styrene, nucleus substituted styrene, acrylonitrile, vinyl chloride, vinylidene chloride, vinyl pyridine, N-vinyl pyrrolidone, vinyl sulfonic acid, fatty acid vinyl, α,β-ethylenically unsaturated carboxylic acids, an alkyl ester of (meth) acrylic acid in which an alkyl group has 1 to 18 carbon atoms, a hydroxyalkyl ester of (meth)acrylic acid in which a hydroxyalkyl group has 1 to 18 carbon atoms, an aminoalkyl ester of (meth)acrylic acid in which an aminoalkyl group has 1 to 18 carbon atoms, an ether oxygen-containing alkyl ester of (meth)acrylic acid in which an ether oxygen-containing alkyl group has 3 to 18 carbon atoms, N-vinylacetamide, p-t-butyl vinyl benzoate, vinyl N,N-dimethylaminobenzoate, vinyl benzoate, vinyl pivalate, vinyl 2,2-dimethylbutanoate, vinyl 2,2-dimethylpentanoate, vinyl 2-methyl-2-butanoate, vinyl propionate, vinyl stearate, vinyl 2-ethyl-2-methylbutanoate, dicyclopentanyloxyethyl (meth)acrylate, isobornyloxylethyl (meth)acrylate, isobornyl (meth)acrylate, adamantyl (meth)acrylate, dimethyladamantyl (meth)acrylate, dicyclopentanyl (meth)acrylate, dicyclopentenyl (meth)acrylate, 2-acryloyloxyethyl succinic acid, 2-acryloyloxyethyl hexahydrophthalic acid, 2-acryloyloxyethylphthalic acid, 2-acryloyloxyethyl-2-hydroxyethylphthalic acid, 2-acryloyloxyethyl acid phosphate, 2-methacryloyloxyethyl acid phosphate, a mono(meth)acrylate ester or a di(meth) acrylic acid ester of a polyalkylene glycol such as a copolymer of polyethylene glycol, polypropylene glycol, or ethylene oxide with a propylene oxide with a degree of polymerization of 2 to 100, or a mono(meth)acrylate ester of a polyalkylene glycol which is a copolymer of a polyethylene glycol, a polypropylene glycol or ethylene oxide with propylene oxide which has a terminal capped with an alkyl group having 1 to 6 carbon atoms and has a degree of polymerization of 2 to 100 are non-liquid crystalline polymerizable compounds which are a monofunctional compound. Vinyl acetate is "fatty acid vinyl." Acrylic acid, methacrylic acid, maleic acid, fumaric acid, and itaconic acid are "α,β-ethylenically unsaturated carboxylic acids." Methoxyethyl ester, ethoxyethyl ester, methoxypropyl ester, methylcarbyl ester, ethyl carbyl ester, and butyl carbyl ester are "ether oxygen-containing alkyl esters of (meth)acrylic acid in which an ether oxygen-containing alkyl group has 3 to 18 carbon atoms."

1,4-Butanediol diacrylate, 1,6-hexanediol diacrylate, 1,9-nonanediol diacrylate, neopentyl glycol diacrylate, dimethylol tricyclodecane diacrylate, triethylene glycol diacrylate, dipropylene glycol diacrylate, tripropylene glycol diacrylate, tetraethylene glycol diacrylate, bisphenol A, diacrylate EO-adducts, bisphenol A glycidyl diacrylate, polyethylene glycol diacrylate, and a methacrylate compound of these compounds are non-liquid crystalline polymerizable compounds which are a bifunctional compound.

Pentaerythritol triacrylate, trimethylolpropane triacrylate, trimethylol EO-adduct triacrylate, tris acryloyloxyethyl phosphate, tris(acryloyloxyethyl) isocyanurate, alkyl-modified dipentaerythritol triacrylate, EO-modified trimethylolpropane triacrylate, PO-modified trimethylolpropane triacrylate, pentaerythritol tetraacrylate, alkyl-modified dipentaerythritol tetraacrylate, ditrimethylolpropane tetraacrylate, dipentaerythritol hexaacrylate, dipentaerythritol monohydroxypentaacrylate, alkyl-modified dipentaerythritol pentaacrylate, pentaerythritol trimethacrylate, trimethylolpropane trimethacrylate, trimethylol EO-adduct trimethacrylate, trismethacryloyloxyethyl phosphate, trismethacryloyloxyethyl isocyanurate, alkyl-modified dipentaerythritol trimethacrylate, EO-modified trimethylolpropane trimethacrylate, PO-modified trimethylolpropane trimethacrylate, pentaerythritol tetramethacrylate, alkyl-modified dipentaerythritol tetramethacrylate, ditrimethylolpropane tetramethacrylate, dipentaerythritol hexamethacrylate, dipentaerythritol monohydroxypentamethacrylate, and alkyl-modified dipentaerythritol pentamethacrylate are non-liquid crystalline polymerizable compounds which are multi-functional compounds which are not a bifunctional compound. When a polymerizable compound having a bisphenol structure or a cardo structure is added to the polymerizable liquid crystal composition, a degree of curing of a polymer is improved and homeotropic alignment of the liquid crystal polymerized film is induced.

Compounds represented by Formula (α-1) to Formula (α-3) are polymerizable fluorene derivatives having a cardo structure.

[Chem. 22]

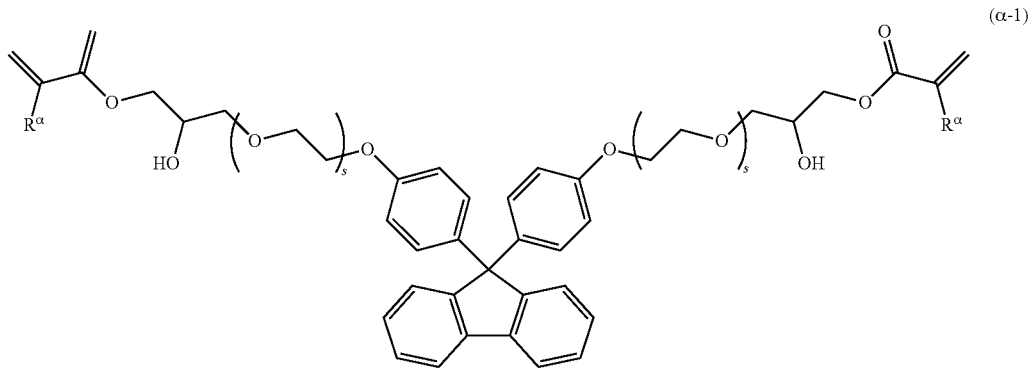

(α-1)

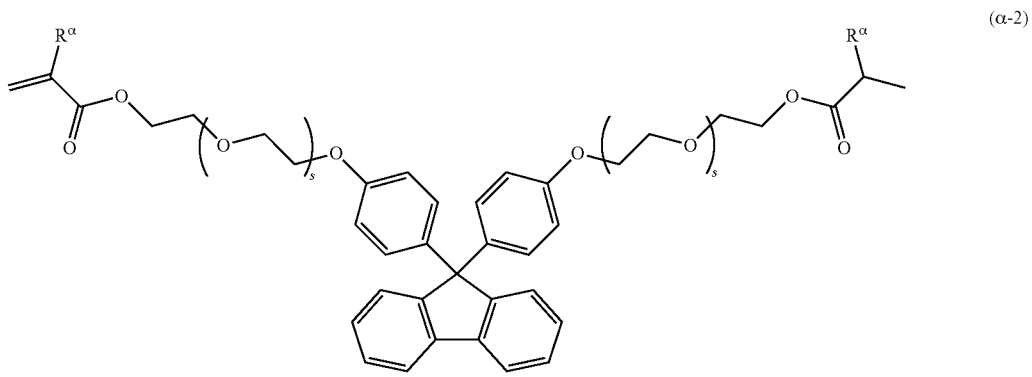

(α-2)

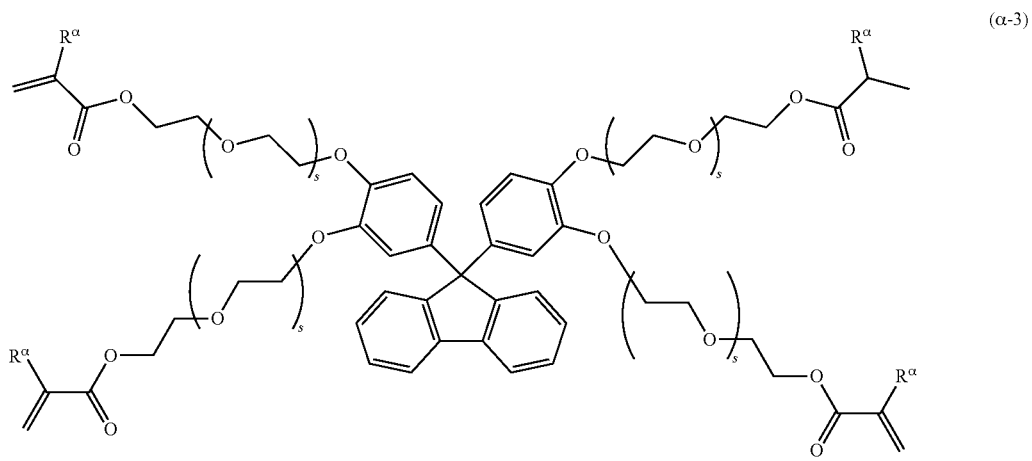

(α-3)

In Formula (α-1) to Formula (α-3), R^α is independently hydrogen or methyl, and s is independently an integer of 0 to 4.

When a polymerization initiator is added, a polymerization rate of the polymerizable liquid crystal composition is optimized. A photo-radical initiator may be the polymerization initiator.

1-hydroxy-cyclohexyl-phenyl-ketone, 2-hydroxy-2-methyl-1-phenylpropan-1-one, 1-hydroxycyclohexyl phenyl ketone, 2,2-dimethoxy-1,2-diphenylethan-1-one, p-methoxyphenyl-2,4-bis(trichloromethyl)triazine, 2-(p-butoxystyryl)-5-trichloromethyl-1,3,4-oxadiazole, 9-phenylacridine, 9,10-benzphenazine, benzophenone/Michler's ketone mixture, hexaarylbiimidazole/mercaptobenzimidazole mixture, 1-(4-isopropylphenyl)-2-hydroxy-2-methyl-propan-1-one, benzyl dimethyl ketal, 2-methyl-1-[4-(methylthio)phenyl]-2-morpholinopropane-1-one, 2,4-diethyl xanthone/p-dimethylaminobenzoate methyl mixture, benzophenone/methyltriethanolamine mixture, Adeka Optomer N-1919, Adeka Cruise NCI-831, Adeka Cruise NCI-930, Irgacure 127, Irgacure 369, Irgacure 379, Irgacure 500, Irgacure 754, Irgacure 784, Irgacure 819, Irgacure 907, Irgacure 1300, Irgacure 1700, Irgacure 1800, Irgacure 1850, Irgacure 1870, Irgacure 2959, Irgacure OXE01, Irgacure OXE02, Darocur 4265, Darocur MBF, and Darocur TPO may be the photo-radical initiators. Here, Adeka, Irgacure, and Darocur are registered trademarks.

In consideration of the contrast of the liquid crystal polymerized film, stickiness prevention, and prevention of temporal change of retardation, a total content by weight of a photo-radical polymerization initiator in the polymerizable liquid crystal composition is preferably 0.01 to 10% by weight, more preferably 0.1 to 4% by weight, and most preferably 0.5 to 4% by weight based on a total amount of the polymerizable liquid crystal composition.

A sensitizer may be added to the polymerizable liquid crystal composition together with the photo-radical polymerization initiator. Isopropyl thioxanthone, diethyl thioxanthone, ethyl-4-dimethylaminobenzoate, and 2-ethylhexyl-4-dimethylaminobenzoate may be the sensitizers.

When a chain transfer agent is added to the polymerizable liquid crystal composition, it is possible to adjust a reaction rate of the polymerizable liquid crystal compound and a length of a chain of a polymer in the liquid crystal polymerized film.

When an amount of the chain transfer agent increases, a reaction rate of the polymerizable liquid crystal compound decreases. When an amount of the chain transfer agent increases, a length of a chain of the polymer decreases.

A thiol derivative and a styrene dimer derivative may be the chain transfer agents.

A thiol derivative which is a monofunctional compound and a thiol derivative which is a multi-functional compound may be the thiol derivatives.

Dodecanethiol and 2-ethylhexyl-(3-mercapto)propionate are thiol derivatives which are a monofunctional compound. Trimethylolpropane tris(3-mercaptopropionate), pentaerythritol tetrakis(3-mercaptopropionate), 1,4-bis(3-mercaptobutyryloxy)butane, pentaerythritol tetrakis(3-mercaptobutyrate), and 1,3,5-tris(3-mercaptobutyloxyethyl)-1,3,5-triazine-2,4,6(1H,3H,5H)-trione are thiol derivatives which are a multi-functional compound.

2,4-diphenyl-4-methyl-1-pentene, and 2,4-diphenyl-1-butene are styrene dimer chain transfer agents.

When a polymerization inhibitor is added to the polymerizable liquid crystal composition, polymerization initiation during storage of the polymerizable liquid crystal composition is prevented. A phenol derivative, a phenothiazine derivative, a compound having a nitroso group, and a benzothiazine derivative may be the polymerization inhibitors. 2,5-di(t-butyl)hydroxytoluene, hydroquinone, o-hydroxybenzophenone, methylene blue, and diphenyl picric acid hydrazide are polymerization inhibitors which are a phenol derivative. Phenothiazine is a polymerization inhibitor which is a phenothiazine derivative. N,N-dimethyl-4-nitrosoaniline is a polymerization inhibitor which is a compound having a typical nitroso group.

When a polymerization inhibitor is added to the polymerizable liquid crystal composition, a polymerization reaction in the polymerizable liquid crystal composition due to generation of radicals in the polymerizable liquid crystal composition is prevented. When a polymerization inhibitor is added, storability of the polymerizable liquid crystal composition is improved.

(a) a phenol-based antioxidant, (b) a sulfur-based antioxidant, (c) a phosphate-based antioxidant, and (d) a hindered amine-based antioxidant are polymerization inhibitors. In consideration of compatibility with the polymerizable liquid crystal composition and transparency of the liquid crystal polymerized film, a phenol-based antioxidant is preferable. In consideration of compatibility, a phenol-based antioxidant having a t-butyl group at the ortho position relative to a hydroxyl group is preferable.

When a UV absorber is added to the polymerizable liquid crystal composition, weatherability of the polymerizable liquid crystal composition is improved.

When a light stabilizer is added to the polymerizable liquid crystal composition, weatherability of the polymerizable liquid crystal composition is improved.

When an antioxidant is added to the polymerizable liquid crystal composition, weatherability of the polymerizable liquid crystal composition is improved.

When a silane coupling agent is added to the polymerizable liquid crystal composition, adhesiveness between the substrate and the liquid crystal polymerized film is improved.

In order to facilitate application, a solvent is preferably added to the polymerizable liquid crystal composition.

An ester, an amide compound, an alcohol, an ether, a glycol monoalkyl ether, an aromatic hydrocarbon, a halogenated aromatic hydrocarbon, an aliphatic hydrocarbon, a halogenated aliphatic hydrocarbon, an alicyclic hydrocarbon, a ketone, and an acetate solvent may be the solvent component.

The amide compound refers to a compound having an amide group and serves as a solvent component. The acetate solvent refers to a compound having an acetate structure and serves as a solvent component.

Alkyl acetates, ethyl trifluoroacetate, alkyl propionates, alkyl butyrates, dialkyl malonates, alkyl glycolates, alkyl lactates, monoacetin, γ-butyrolactone, and γ-valerolactone may be the ester.

Methyl acetate, ethyl acetate, propyl acetate, isopropyl acetate, butyl acetate, 3-methoxybutyl acetate, isobutyl acetate, pentyl acetate, and isopentyl acetate are "alkyl acetates." Methyl propionate, methyl 3-methoxypropionate, ethyl propionate, propyl propionate, and butyl propionate are "alkyl propionates." Methyl butyrate, ethyl butyrate, butyl butyrate, isobutyl butyrate, and propyl butyrate are "alkyl butyrates." Diethyl malonate is a "dialkyl malonate." Methyl glycolate and ethyl glycolate are "alkyl glycolates." Methyl lactate, ethyl lactate, isopropyl lactate, n-propyl lactate, butyl lactate, and ethylhexyl lactate are "alkyl lactates."

N-methyl-2-pyrrolidone, N,N-dimethylacetamide, N-methylpropionamide, N,N-dimethylformamide, N,N-diethylformamide, N,N-diethylacetamide, N,N-dimethylacetamide dimethyl acetal, N-methylcaprolactam, and dimethylimidazolidinone may be the amide compound.

Methanol, ethanol, 1-propanol, 2-propanol, 1-methoxy-2-propanol, t-butyl alcohol, sec-butyl alcohol, butanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerin, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol, and methylcyclohexanol may be the alcohol.

Ethylene glycol dimethyl ether, diethylene glycol dimethyl ether, bis(2-propyl)ether, 1,4-dioxane, and tetrahydrofuran may be the ether.

Ethylene glycol monoalkyl ether, diethylene glycol monoalkyl ether, triethylene glycol monoalkyl ether, propylene glycol monoalkyl ether, dipropylene glycol monoalkyl ether, ethylene glycol monoalkyl ether acetate, diethylene glycol monoalkyl ether acetate, triethylene glycol monoalkyl ether acetate, propylene glycol monoalkyl ether acetate, dipropylene glycol monoalkyl ether acetate, and diethylene glycol methyl ethyl ether may be the glycol monoalkyl ether.

Ethylene glycol monomethyl ether, and ethylene glycol monobutyl ether may be the ethylene glycol monoalkyl ether. Ethylene glycol monoalkyl ether may be the diethylene glycol monoethyl ether. Propylene glycol monobutyl ether may be the propylene glycol monoalkyl ether. Dipropylene glycol monomethyl ether may be the dipropylene glycol monoalkyl ether. Ethylene glycol monobutyl ether acetate may be ethylene glycol monoalkyl ether acetate. Diethylene glycol monoethyl ether acetate may be diethylene glycol monoalkyl ether acetate. Propylene glycol monomethyl ether acetate, propylene glycol monoethyl ether acetate, and propylene glycol monobutyl ether acetate may be propylene glycol monoalkyl ether acetates. Dipropylene glycol monomethyl ether acetate may be dipropylene glycol monoalkyl ether acetate.

Benzene, toluene, xylene, mesitylene, ethylbenzene, diethylbenzene, i-propylbenzene, n-propylbenzene, t-butylbenzene, s-butylbenzene, n-butylbenzene, and tetralin may be the aromatic hydrocarbon.

The halogenated aromatic hydrocarbon may be chlorobenzene, and the like. Aliphatic hydrocarbons may be hexane and heptane and the like. The halogenated aliphatic hydrocarbons may be chloroform, dichloromethane, carbon tetrachloride, dichloroethane, trichlorethylene, and tetrachlorethylene. Alicyclic hydrocarbons may be cyclohexane and decalin.

Ketones may be acetone, methyl ethyl ketone, methyl isobutyl ketone, cyclohexanone, cyclopentanone, and methyl propyl ketone.

Acetate solvents may be ethylene glycol monomethyl ether acetate, propylene glycol monomethyl ether acetate, propylene glycol monoethyl ether acetate, methyl acetoacetate, and 1-methoxy-2-propyl acetate.

In consideration of compatibility with the polymerizable liquid crystal compound, there is preferably 30 to 96% by weight, more preferably 50 to 90% by weight, and most preferably 60 to 80% by weight of a solvent in the polymerizable liquid crystal composition with respect to a total amount of the polymerizable liquid crystal composition.

The polymerizable liquid crystal composition of the present invention may contain a compound having optical activity. When a compound having optical activity is added to the liquid crystal composition, the liquid crystal polymerized film is induced to have twist alignment. The liquid crystal polymerized film can be used as a selective reflection film in a wavelength region of 300 to 2000 nm and a negative type C plate.

As the compound having optical activity, a compound including an asymmetric carbon atom, an axially asymmetric compound having a binaphthyl structure and a helicene structure, and a plane asymmetric compound having a cyclophane structure may be exemplified. In consideration of fixing a helical pitch of twist alignment, a compound having optical activity in this case is preferably a polymerizable compound.

The liquid crystal polymerized film of the present invention may contain a dichroic dye. A liquid crystal polymerized film complexed with a dichroic dye can be used as an absorptive polarizing plate.

A dichroic dye having a maximum absorption wavelength in a range of 300 to 700 nm is preferable. Acridine dyes, oxazine dyes, cyanine dyes, naphthalene dyes, azo dyes, and anthraquinone dyes can be used. As azo dyes, monoazo dyes, bisazo dyes, trisazo dyes, tetrakisazo dyes, and stilbene azo dyes are dichroic dyes.

The liquid crystal polymerized film of the present invention may contain a fluorescent dye. A liquid crystal polymerized film complexed with a fluorescent dye can be used as a polarized light emitting film and a wavelength conversion film.

<Substrate>

A glass, a plastic, and a metal are a material of a substrate. A surface of the glass or the metal may be processed into a slit shape. The plastic may be subjected to a surface treatment such as a stretching treatment, a hydrophilic treatment, and a hydrophobic treatment.

When a liquid crystal polymerized film having homogeneous alignment and tilt alignment is formed on a substrate, before the polymerizable liquid crystal composition is applied to the substrate, a surface treatment is performed on the substrate to induce alignment of the liquid crystal polymerized film. As the surface treatment, methods of (a) rubbing a substrate, (b) obliquely depositing silicon oxide on a substrate, and (c) providing a polymer coating on a substrate and emitting polarized UV to the polymer coating may be exemplified.

The following procedures are an example of (a) rubbing a substrate.

(1) A rubbing cloth made of a material such as rayon, cotton, or polyamide is wound around a metal roller, (2) The roller is brought into contact with a substrate, and (3) The roller is moved parallel to a surface of the substrate while rotating the roller or the substrate is moved while the roller is fixed.

Before rubbing, a polymer coating may be provided on the substrate, and rubbing may be performed on the coating. As the coating, a coating called a rubbing alignment film of polyimide, polyamic acid, or polyvinyl alcohol is used.

According to rubbing, it is possible to prevent an alignment defect of the liquid crystal polymerized film with a substrate.

The following procedures are an example of (c) providing a polymer coating on a substrate and emitting polarized UV to the polymer coating.

(1) A polymer coating called a photoalignment film is provided on a substrate, (2) Linearly polarized light having a wavelength of 250 to 400 nm is emitted to the substrate, and (3) A heat treatment is performed as necessary.

The photoalignment film has a photosensitive group and contains a polyimide, polyamic acid, or polyacrylate. The photosensitive group is a functional group that causes a chemical reaction according to light absorption. A structural change resulting from isomerization, dimerization, transition, decomposition, or another photoexcitation is the chemical reaction. Since it is possible to prepare a photoalignment film with a small amount of polarized UV emitted, the photosensitive group is preferably a functional group having a chalcone skeleton, a cinnamoyl skeleton, a stilbene skeleton, a cyclobutane skeleton, or an azobenzene skeleton. According to polarized UV emission, it is possible to prevent an alignment defect of the liquid crystal polymerized film and it is possible to prevent an alignment defect due to scraping by rubbing.

<Liquid Crystal Polymerized Film with Substrate>

The liquid crystal polymerized film of the present invention with a substrate is obtained according the following processes.

(1) A polymerizable liquid crystal composition is applied onto a substrate and, as necessary, dried to form a coating film.

(2) While the polymerizable liquid crystal composition is aligned, polymerization occurs according to a method using light, heat, or a catalyst, and a liquid crystal polymerized film with a substrate is obtained.

Accordingly, the polymerizable liquid crystal composition in the coating film is fixed while maintaining alignment in a liquid crystal state.

Various coating methods are used for applying a polymerizable liquid crystal composition. In consideration of uniformity of a film thickness of the polymerizable liquid crystal composition on the substrate, as a coating method, a spin coating method, a micro gravure coating method, a gravure coating method, a wire bar coating method, a dip coating method, a spray coating method, a meniscus coating method, and a die coating method are preferable.

In order to remove a solvent, a heat treatment is preferably performed during drying when the liquid crystal polymerized film with a substrate is formed. The heat treatment can be performed using a hot plate, a drying furnace, and warm air or hot air blowing.

In order to obtain the liquid crystal polymerized film of the present invention, means such as an electron beam, ultraviolet light, visible light, and infrared radiation can be used. A wavelength range of the radiation emitted in order to obtain the liquid crystal polymerized film is 150 to 500 nm. A preferable light wavelength range is 250 to 450 nm, and a more preferable range is 300 to 400 nm.

As a light source of the light, a low pressure mercury lamp, a high pressure discharge lamp, and a short arc discharge lamp can be used. The low pressure mercury lamp may be a sterilization lamp, a fluorescent chemical lamp, and a black light. The high pressure discharge lamp may be a high pressure mercury lamp and a metal halide lamp. The short arc discharge lamp may be an ultra high pressure mercury lamp, a xenon lamp, and a mercury xenon lamp.

The liquid crystal polymerized film can be disposed inside or outside a liquid crystal cell of a liquid crystal display device. The liquid crystal polymerized film can be disposed inside the liquid crystal cell because then variation in retardation of the liquid crystal polymerized film due to a thermal history is small and an amount of impurities eluted from the liquid crystal polymerized film to a liquid crystal is small.

When the liquid crystal polymerized film is formed using a polarizing plate as a substrate, it is possible to produce a polarizing plate having a function such as optical compensation. For example, when a liquid crystal polymerized film having retardation of ¼ wavelength and a polarizing plate are combined, a circularly polarizing plate can be produced.

An absorptive polarizing plate doped with iodine or a dichroic dye and a reflective polarizing plate such as a wire grid polarizing plate are polarizing plates.

As a method of removing a liquid crystal polymerized film from a liquid crystal polymerized film with a substrate and fixing it on another substrate, the following method is known.

(1) A liquid crystal polymerized film with a substrate and a basal plate including a pressure-sensitive adhesive layer are bonded together so that the liquid crystal polymerized film and the pressure-sensitive adhesive layer are in contact with each other, (2) A part in which the liquid crystal polymerized film and the pressure-sensitive adhesive layer are bonded together and in contact with each other is separated between the substrate part of the liquid crystal polymerized film with a substrate and the liquid crystal polymerized film, and (3) The liquid crystal polymerized film on the substrate including the pressure-sensitive adhesive layer is fixed to another substrate in the same manner as in the above (1) and (2).

EXAMPLES

The scope of the present invention is not limited to only these examples.

<Definition of Terms>

In the examples of the present invention, "DCC" is 1,3-dicyclohexylcarbodiimide.

In the examples of the present invention, "DMAP" is 4-dimethylaminopyridine.

In the examples of the present invention, "pTSA" is p-toluene sulfonic acid.

<Obtaining Reagents>

In the examples of the present invention, "Irg-907" is Irgacure (trademark) 907 (commercially available from BASF Japan).

In the examples of the present invention, "NCI-930" is Adeka Cruise (trademark) NCI-930 (commercially available from ADEKA).

In the examples of the present invention, "FTX-218" is Ftergent (trademark) FTX-218 (commercially available from Neos Corporation).

In the examples of the present invention, "TF370" is TEGOFlow (trademark) 370 (commercially available from Evonik Japan).

In the examples of the present invention, "Polyflow No. 75" is Polyflow (trademark) No. 75 (commercially available from Kyoeisha Chemical Co., Ltd.).

In the examples of the present invention, "polystyrene with a known molecular weight" is a part number 0006476 (commercially available from Tosoh Corporation).

In the examples of the present invention, "palladium carbon" is P1528 (commercially available from Tokyo Chemical Industry Co., Ltd.).

<Devices Used to Determine a Structure and the Like>

In the examples of the present invention, NMR measurement was performed using a DRX-500 (commercially available from Broker Corporation).

In the examples of the present invention, gel permeation chromatography analysis was performed using an LC-9A model (commercially available from Shimadzu Corporation).

In the examples of the present invention, the gel permeation chromatography column was a Shodex (trademark) GF-7M HQ.

<Devices Used to Measure Optical Properties and the Like>

In the examples of the present invention, a polarization microscope was an ECLIPSE E600 POL (commercially available from Nikon Corporation).

In the examples of the present invention, a polarization analyzer was an OPIPRO polarization analyzer (commercially available from Shintec Co., Ltd.).

In the examples of the present invention, a luminance meter was YOKOGAWA 3298F.

In the examples of the present invention, a wire grid polarizing plate was UVT300A (commercially available from Polatechno Co., Ltd.).

In the examples of the present invention, "an optical receiver for measuring an illuminance at a wavelength of about 313 nm" was a UVD-S313 (commercially available from Ushio Inc.).

In the examples of the present invention, "an optical receiver for measuring illuminance of a wavelength of about 365 nm" was UVD-S365 (commercially available from Ushio Inc.).

<Devices Used to Measure Other Values>

In the examples of the present invention, a melting point measuring device was a system including a temperature controller FP90 and a heating stage FP82 (commercially available from Mettler Toledo).

In the examples of the present invention, level differences between parts of a liquid crystal polymerized film was measured using an Alpha Step IQ (commercially available from KLA TENCOR).

<Prototype Device>

In the examples of the present invention, an ultra-high pressure mercury lamp was multi-light USH-250BY (commercially available from Ushio Inc.).

In the examples of the present invention, an ultraviolet illuminometer was UIT-150-A (commercially available from Ushio Inc.).

In the examples of the present invention, an optical receiver for measuring illuminance of a wavelength of about 313 nm was UVD-S313 (commercially available from Ushio Inc.).

In the examples of the present invention, an optical receiver for measuring illuminance of a wavelength of about 365 nm was UVD-S365 (commercially available from Ushio Inc.).

<Determination of Structure and the Like>

A structure of a compound was determined by dissolving a compound to be analyzed in $CDCl_3$ and analyzing the solution using $^1$H-NMR at 500 MHz. An actual measurement value of NMR was obtained by omitting a unit ppm from a value of a shift based on TMS. In notation of the actual measurement values of NMR, s is a singlet, d is a doublet, t is a triplet, and m is a multiplet.

<Measurement of Weight Average Molecular Weight>

A weight average molecular weight was determined according to gel permeation chromatography. A temperature of the column during elution was set to 40° C. THF was used as an eluting solvent for gel permeation chromatography. In this case, polystyrene with a known molecular weight was used as a standard material for determining a weight average molecular weight.

<Measurement of Optical Properties and the Like>
<Visual Observation Method>

The presence or absence of an alignment defect was determined when a substrate on which a retardation film was formed was interposed between two polarizing plates disposed in crossed nicols. The substrate was rotated within a horizontal plane, and a light or dark state was visually confirmed. When there was a part in which light appeared to be missing in a dark state or when neither a light state nor a dark state was confirmed, it was determined that an alignment defect was "present." When an alignment defect was not "present," it was determined that there was "no" alignment defect.

<Measurement by Polarization Analyzer>

Retardation of the liquid crystal polymerized film was measured with a light incident angle of 0° using a polarization analyzer. A wavelength of light used for measuring retardation was 550 nm.

<Determination of Homogeneous Alignment>

Retardation was measured by changing a light incident angle with respect to a surface of the liquid crystal polymerized film from −50° to 50° in increments of 5° using a polarization analyzer. Here, a tilt direction of the light incident angle was the same as a slow axis of the liquid crystal polymerized film. When both of the following conditions were satisfied, the liquid crystal polymerized film was considered to be homogeneously aligned.

(a) A condition in which retardation with respect to an incident angle of the liquid crystal polymerized film is convex upward, and (b) a condition in which a difference between measurement values of Re when absolute values of incident angles are the same is within 5%.

<Evaluation of Birefringence>

Birefringence was calculated by (retardation)/(film thickness).

<Measurement of Luminance in Crossed Nicols State>

A luminance in a crossed nicols state was measured according to the following procedures.

(1) A liquid crystal polymerized film with a substrate was interposed between two polarizing plates and both the polarizing plates were disposed in a luminance meter so that they became crossed nicols, and (2) A luminance that was a minimum when the substrate was rotated horizontally was obtained as "luminance in a crossed nicols state."

<Measurement of Luminance in Parallel Nicols State>

Luminance in a parallel nicols state was measured according to the following procedures.

(1) A liquid crystal polymerized film with a substrate was interposed between two polarizing plates and the both polarizing plates were disposed in a luminance meter so that they became parallel nicols, and (2) luminance that was a maximum when the substrate was rotated horizontally was obtained as "luminance in a parallel nicols state."

<Measurement of Phase Transition Temperature>

A transition temperature was measured as follows. A sample was placed on a hot plate of the melting point measuring device and a transition temperature was measured under the polarization microscope. The transition temperature was measured while heating at a rate of 3° C./min.

<Measurement of Film Thickness>

A film thickness of a liquid crystal polymerized film having a glass substrate was measured according to the following procedures.

(1) a liquid crystal polymerized film was cut out from a glass substrate of a liquid crystal polymerized film, (2) a step difference between a part including the liquid crystal polymerized film and a part excluding the liquid crystal polymerized film was measured, and (3) the measurement value was obtained as a film thickness.

<Preparation of Samples>

<Preparation of Light Alignment Agent>

A polymer represented by Formula (J) was synthesized in the same manner as in Example 9 in Japanese Unexamined Patent Application Publication No. 2012-087286.

[Chem. 23]

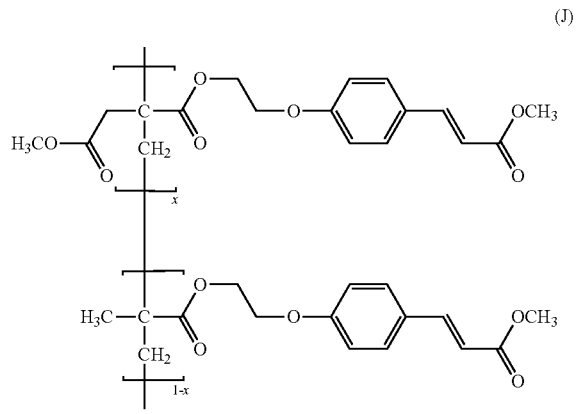

In Formula (J), x was 0.1, and a weight average molecular weight was 53,700. A product obtained by dissolving 5% by weight of the polymer represented by Formula (J) in 95% by weight of cyclopentanone and filtering it through a filter was named a light alignment agent (1).

<Preparation of Photoalignment Film>

A glass substrate with an alignment film was prepared according to the following procedures.

Procedure (1) in which the light alignment agent (1) was spin-coated on a glass to prepare a coating film.

Procedure (2) in which a substrate having a coating film was left on a hot plate at 100° C. for 60 seconds, and a solvent was removed from the coating film.

Procedure (3) in which linearly polarized ultraviolet light with a constant output was emitted to the coating film on the substrate in a direction of 90° at room temperature to prepare a glass substrate with an alignment film.

This was provided that linearly polarized ultraviolet light in the procedure (3) was obtained by light from the ultra-high pressure mercury lamp being transmitted through the wire grid polarizing plate. In addition, using an optical receiver for measuring illuminance of a wavelength of about 313 nm, an emission time in the procedure (3) was adjusted to between 20 seconds and 40 seconds so that an amount of linearly polarized ultraviolet light with which a surface of the coating film on the substrate was exposed in the procedure (3) was 200 mJ/cm$^2$.

EXAMPLES

A compound (1-1-3-1) was synthesized according to the following procedure.

[Chem. 24]

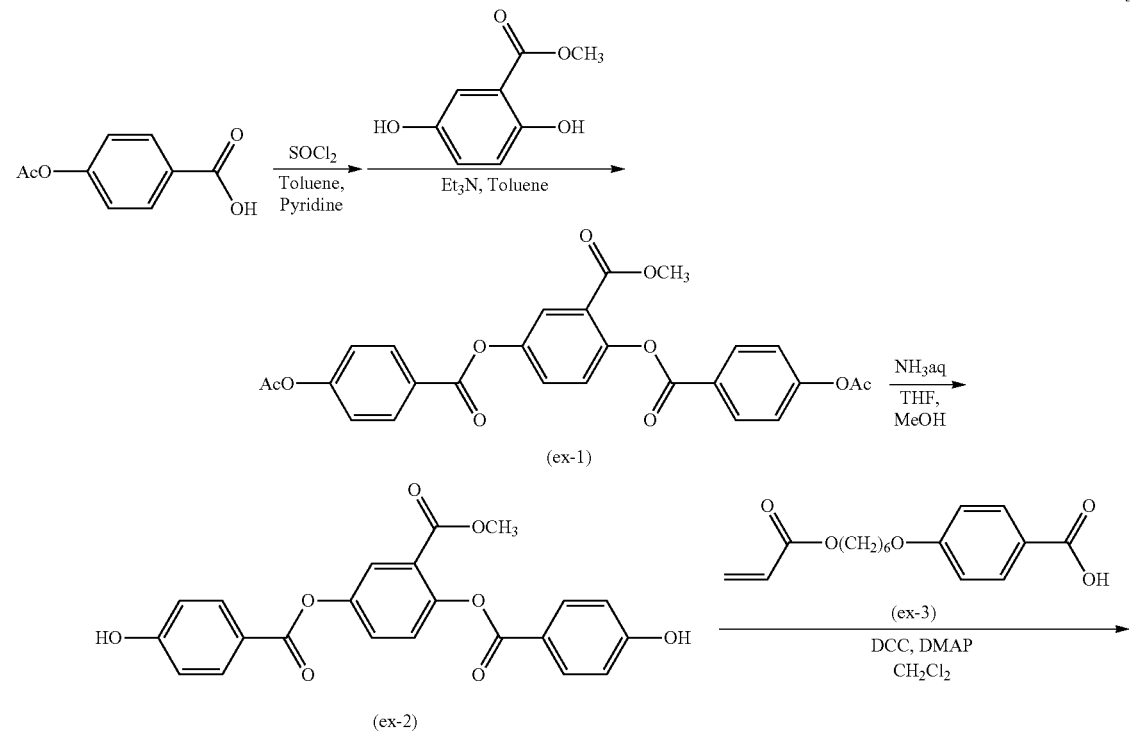

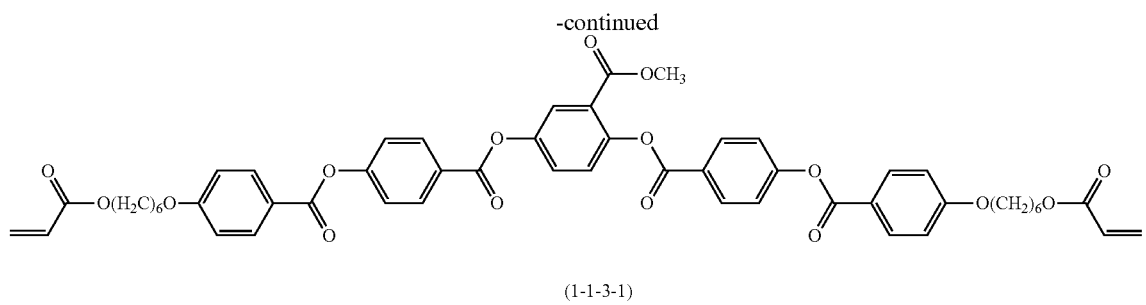

(1-1-3-1)

42.9 g of 4-acetoxybenzoic acid and 0.2 g of pyridine were added to 430 mL of toluene and stirring was performed under a nitrogen atmosphere at 60° C. 34.0 g of thionyl chloride was added dropwise thereto. After dropwise addition, stirring was performed at 60° C. for 4 hours. Toluene was distilled off under a reduced pressure. The obtained residue was added to 230 mL of toluene and stirred while cooling under a nitrogen atmosphere. A 200 mL toluene solution in which 20.0 g of methyl 2,5-dihydroxybenzoate and 33.7 g of triethylamine were dissolved was added dropwise thereto. After dropwise addition, stirring was performed for 4 hours at room temperature. Water was added to the stirred solution and an organic layer was extracted. Next, the organic layer was washed with water and dried with anhydrous magnesium sulfate. Toluene was distilled off under a reduced pressure, and the residue was purified through column chromatography and recrystallization was performed with a mixture (v/v=1/4) of ethyl acetate and heptane to obtain 42.9 g of a compound (ex-1). Here, the packing of the chromatography column was silica gel. Here, the eluent was a mixture (v/v=9/1) of toluene and ethyl acetate.

42.9 g of the compound ex-1 and 14 mL of a 28% by weight aqueous ammonia solution were added to a mixed solution containing 86 mL of THF and 43 mL of methanol and stirring was performed for 4 hours at room temperature under a hydrogen atmosphere. Ethyl acetate and saturated saline were added to the reaction solution and an organic layer was extracted. Next, the organic layer was washed with saturated saline and dried with anhydrous magnesium sulfate. A solvent was distilled off under a reduced pressure and recrystallization was performed with a mixture (v/v=1/1) of ethyl acetate and heptane to obtain 24.2 g of a compound (ex-2).

A compound ex-3 was synthesized in the same manner as in Journal of Polymer Science, Part A; Polymer Chemistry, 2011. 49 (3). 770-780.

12.0 g of the compound ex-2, 18.0 g of the compound ex-3 and 1.5 g of DMAP were added to 180 mL of dichloromethane and stirred while cooling in an ice bath at 5° C. under a nitrogen atmosphere. 26 mL of a dichloromethane solution in which 13.0 g of DCC was dissolved was added dropwise thereto. After dropwise addition, stirring was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 22.7 g of a compound (1-1-3-1). Here, the packing of the column chromatography was silica gel. Here, the eluent was a mixture (v/v=14/1) of toluene and ethyl acetate.

A transition temperature of the compound (1-1-3-1) from a crystal phase to a nematic phase was 103° C. A transition temperature of the compound (1-1-3-1) from a nematic phase to an isotonic liquid was not confirmed at 250° C. or less.

Signals of $^1$H-NMR of the compound (1-1-3-1) were as follows.

8.31 (d, 2H), 8.28 (d, 2H), 8.17 (d, 4H), 7.96 (s, 1H), 7.51 (d, 1H), 7.40 (d, 4H), 7.33 (d, 1H), 6.99 (d, 4H), 6.41 (d, 2H), 6.16-6.08 (m, 2H), 5.83 (d, 2H), 4.19 (t, 4H), 4.05 (t, 4H), 3.78 (s, 3H), 1.88-1.81 (m, 4H), 1.77-1.70 (m, 4H), 1.58-1.44 (m, 8H).

A compound (1-1-1-1) was synthesized according to the following procedure.

[Chem. 25]

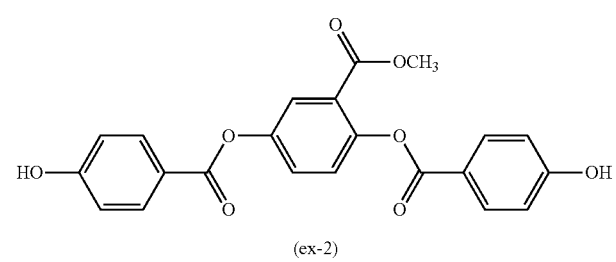

(ex-2)

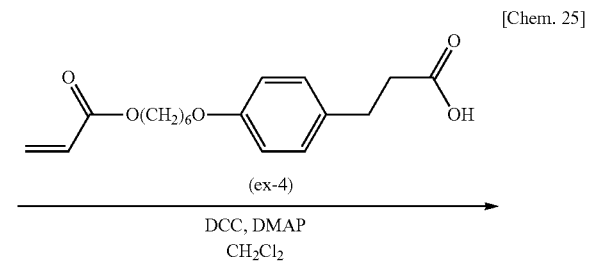

(ex-4)

$\xrightarrow{\text{DCC, DMAP}}$
$\text{CH}_2\text{Cl}_2$

-continued

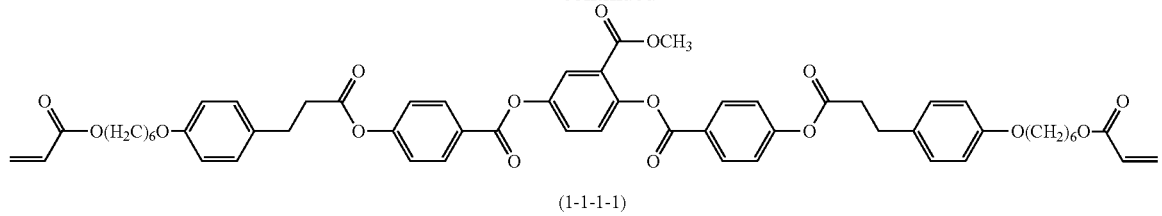

(1-1-1-1)

A compound ex-4 was synthesized in the same manner as in the method in Example 5 in Japanese Unexamined Patent Application Publication No. 2016-047813.

12.0 g of the compound ex-2, 19.3 g of the compound ex-4, and 1.5 g of DMAP were added to 180 mL of dichloromethane, and stirring was performed while cooling in an ice bath at 5° C. under a nitrogen atmosphere. 26 mL of a dichloromethane solution in which 13.0 g of DCC was dissolved was added dropwise thereto. After dropwise addition, stirring was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 19.7 g of a compound (1-1-1-1). Here, the packing of the column chromatography was silica gel. Here, the eluent was a mixture (v/v=14/1) of toluene and ethyl acetate.

A transition temperature of the compound (1-1-1-1) from a crystal phase to a nematic phase was 98° C. A transition temperature of the compound (1-1-1-1) from a nematic phase to an isotonic liquid was 147° C.

Signals of $^1$H-NMR of the compound (1-1-1-1) were as follows.

8.24 (d, 2H), 8.22 (d, 2H), 7.93 (s, 1H), 7.48 (d, 1H), 7.29 (d, 1H), 7.21-7.16 (m, 8H), 6.86 (d, 4H), 6.41 (d, 2H), 6.16-6.08 (m, 2H), 5.83 (d, 2H), 4.17 (t, 4H), 3.96 (t, 4H), 3.76 (s, 3H), 3.04 (t, 4H), 2.90 (t, 4H), 1.84-1.77 (m, 4H), 1.75-1.69 (m, 4H), 1.56-1.42 (m, 8H).

A compound (1-1-5-1) was synthesized according to the following procedure.

[Chem. 26]

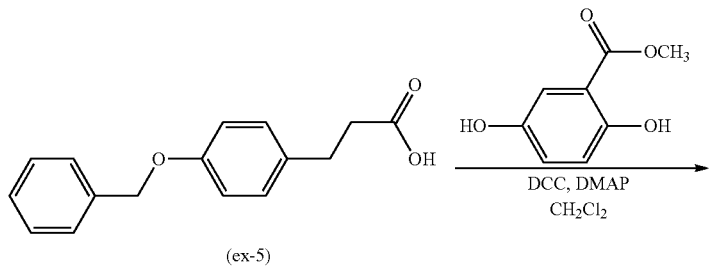

(ex-5)

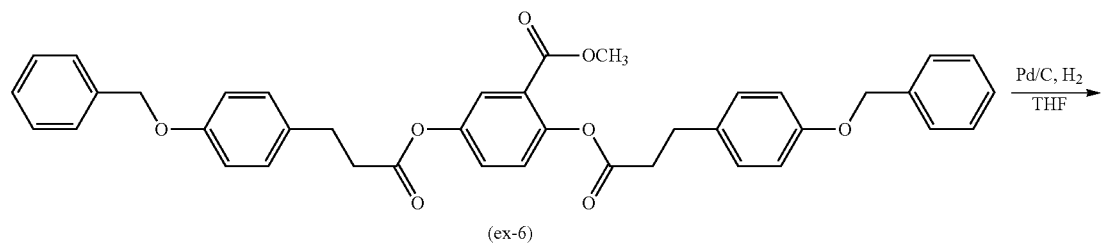

(ex-6)

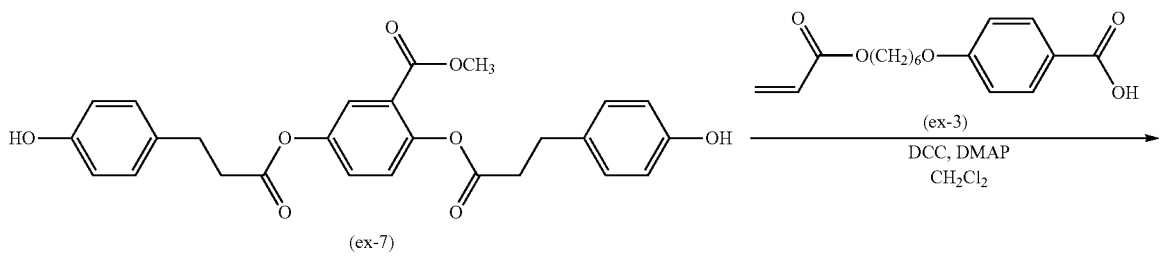

(ex-7)

-continued

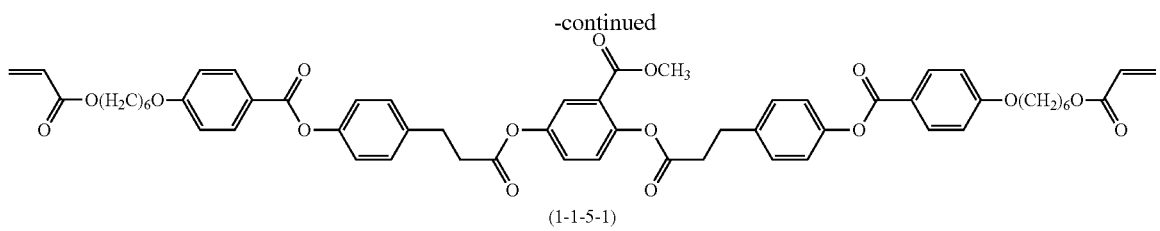

(1-1-5-1)

A compound ex-5 was synthesized in the same manner as in the method in ACS. Medicinal. Chemistry. Letters. 2010. 1(7). 345-349.

68.1 g of the compound ex-5, 21.8 g of methyl 2,5-dihydroxybenzoate and 6.5 g of DMAP were added to 560 mL of dichloromethane, and stirring was performed while cooling in an ice bath at 5° C. under a nitrogen atmosphere. 120 mL of a dichloromethane solution in which 57.6 g of DCC was dissolved was added dropwise thereto. After dropwise addition, stirring was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 74.5 g of a compound (ex-6). Here, the packing of the column chromatography was silica gel. Here, the eluent was a mixture (v/v=20/1) of toluene and ethyl acetate.

74.5 g of the compound ex-6 and 3.7 g of palladium carbon were added to 745 mL of THF and stirring was performed for 24 hours under a hydrogen atmosphere at room temperature. Insoluble substances were separated off by filtration, THF was distilled off under a reduced pressure and drying under a reduced pressure was performed to obtain 53.0 g of a compound (ex-7).

12.9 g of the compound ex-3, 10.0 g of the compound ex-7 and 1.1 g of DMAP were added to 110 mL of dichloromethane, and stirring was performed while cooling in an ice bath at 5° C. under a nitrogen atmosphere. 20 mL of a dichloromethane solution in which 9.6 g of DCC was dissolved was added dropwise thereto. After dropwise addition, stirring was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 8.8 g of a compound (1-1-5-1). Here, the packing of of the column chromatography was silica gel. Here, the eluent was a mixture (v/v=9/1) of toluene and ethyl acetate.

A transition temperature of the compound (1-1-5-1) from a crystal phase to a nematic phase was 83° C. A transition temperature of the compound (1-1-5-1) from a nematic phase to an isotonic liquid was not confirmed because polymerization occurred at about 140° C.

Signals of $^1$H-NMR of the compound (1-1-5-1) were as follows.

8.14 (d, 4H), 7.71 (s, 1H), 7.33 (d, 2H), 7.31 (d, 2H), 7.23 (d, 1H), 7.18-7.14 (m, 4H), 7.04 (d, 1H), 6.97 (d, 4H), 6.41 (d, 2H), 6.16-6.08 (m, 2H), 5.83 (d, 2H), 4.19 (t, 4H), 4.05 (t, 4H), 3.82 (s, 3H), 3.14-3.07 (m, 4H), 2.97 (t, 2H), 2.91 (t, 2H), 1.88-1.81 (m, 4H), 1.77-1.69 (m, 4H), 1.58-1.44 (m, 8H).

A compound (1-1-2-1) was synthesized according to the following procedure.

[Chem. 27]

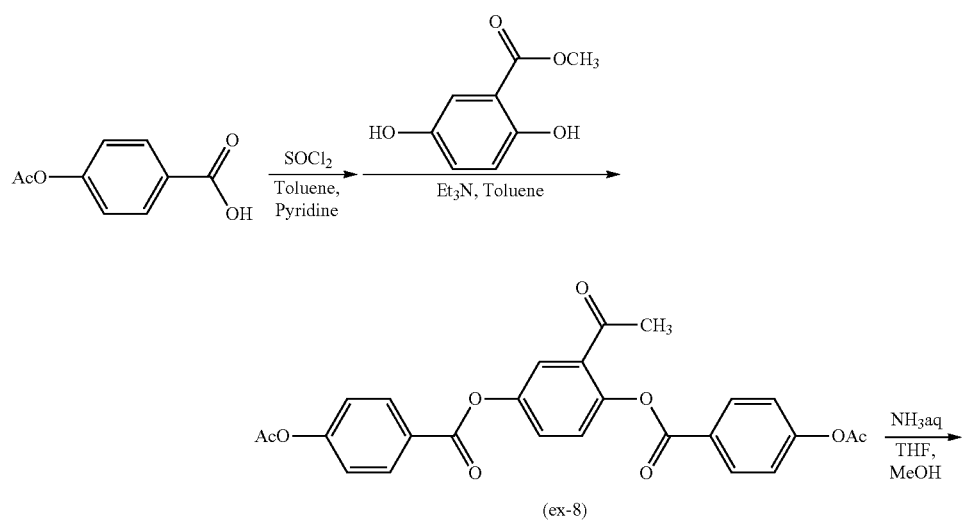

(ex-8)

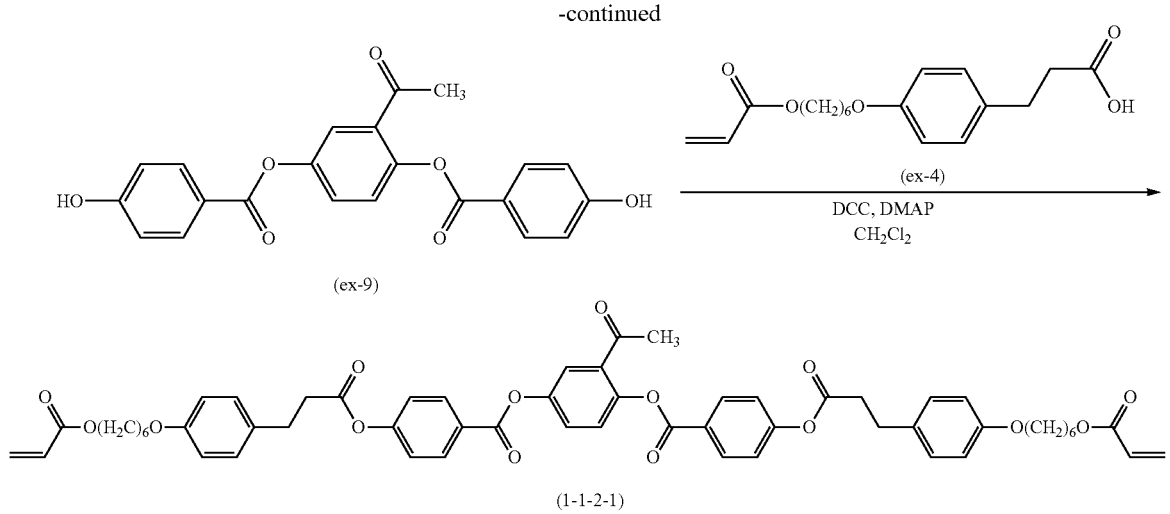

20.0 g of 4-acetoxybenzoic acid and 0.1 g of pyridine were added to 200 mL of toluene, and stirring was performed at 60° C. under a nitrogen atmosphere. 14.5 g of thionyl chloride was added dropwise thereto. After dropwise addition, stirring was performed for 4 hours at 60° C. Toluene was distilled off under a reduced pressure. The obtained residue was added to 200 mL of toluene, and stirred while cooling under a nitrogen atmosphere. 200 mL of a toluene solution in which 8.2 g of methyl 2,5-dihydroxybenzoate and 33.7 g of triethylamine were dissolved was added dropwise thereto. After dropwise addition, stirring was performed for 4 hours at room temperature. Water was added to the stirred solution and an organic layer was extracted. Next, the organic layer was washed with water and dried with anhydrous magnesium sulfate. Toluene was distilled off under a reduced pressure, and the residue was purified through column chromatography and recrystallization was performed with a mixture (v/v=1/4) of ethyl acetate and heptane to obtain 22.0 g of a compound (ex-8). Here, the packing of the column chromatography was silica gel. Here, the eluent was a mixture (v/v=9/1) of toluene and ethyl acetate.

22.0 g of the compound ex-8 and 8 mL of a 28% by weight ammonium aqueous solution were added to a solution mixture containing 44 mL of THF and 22 mL of methanol and stirring was performed for 4 hours at room temperature under a hydrogen atmosphere. Ethyl acetate and saturated saline were added to the reaction solution, and an organic layer was extracted. Next, the organic layer was washed with saturated saline and dried with anhydrous magnesium sulfate. A solvent was distilled off under a reduced pressure and recrystallization was performed with a mixture (v/v=1/1) of ethyl acetate and heptane to obtain 14.9 g of a compound (ex-9).

10.0 g of the compound ex-4, 6.0 g of the compound ex-9, and 0.8 g of DMAP were added to 100 mL of dichloromethane, and stirring was performed while cooling in an ice bath at 5° C. under a nitrogen atmosphere. 14 mL of a dichloromethane solution in which 6.8 g of DCC was dissolved was added dropwise thereto. After dropwise addition, stiffing was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 11.5 g of a compound (1-1-2-1). Here, the packing of the column chromatography was silica gel. Here, the eluent was a mixture (v/v=14/1) of toluene and ethyl acetate.

A transition temperature of the compound (1-1-2-1) from a crystal phase to a nematic phase was 101° C. A transition temperature of the compound (1-1-2-1) from a nematic phase to an isotonic liquid was not confirmed at 152° C. or less.

Signals of $^1$H-NMR of the compound (1-1-2-1) were as follows.

8.24 (d, 2H), 8.22 (d, 2H), 7.92 (s, 1H), 7.47 (d, 1H), 7.29 (d, 1H), 7.21-7.16 (m, 8H), 6.86 (d, 4H), 6.41 (d, 2H), 6.16-6.08 (m, 2H), 5.83 (d, 2H), 4.17 (t, 4H), 3.96 (t, 4H), 3.04 (t, 4H), 2.90 (t, 4H), 2.72 (s, 3H), 1.84-1.77 (m, 4H), 1.75-1.69 (m, 4H), 1.56-1.42 (m, 8H).

A compound (1-2-2-1) was synthesized according to the following procedure.

[Chem. 28]

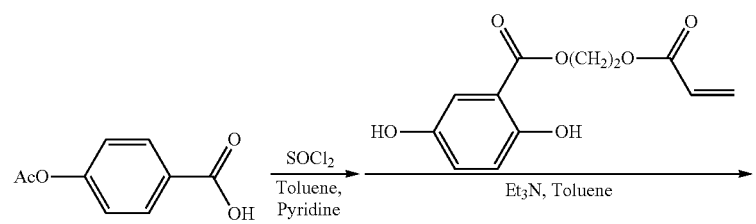

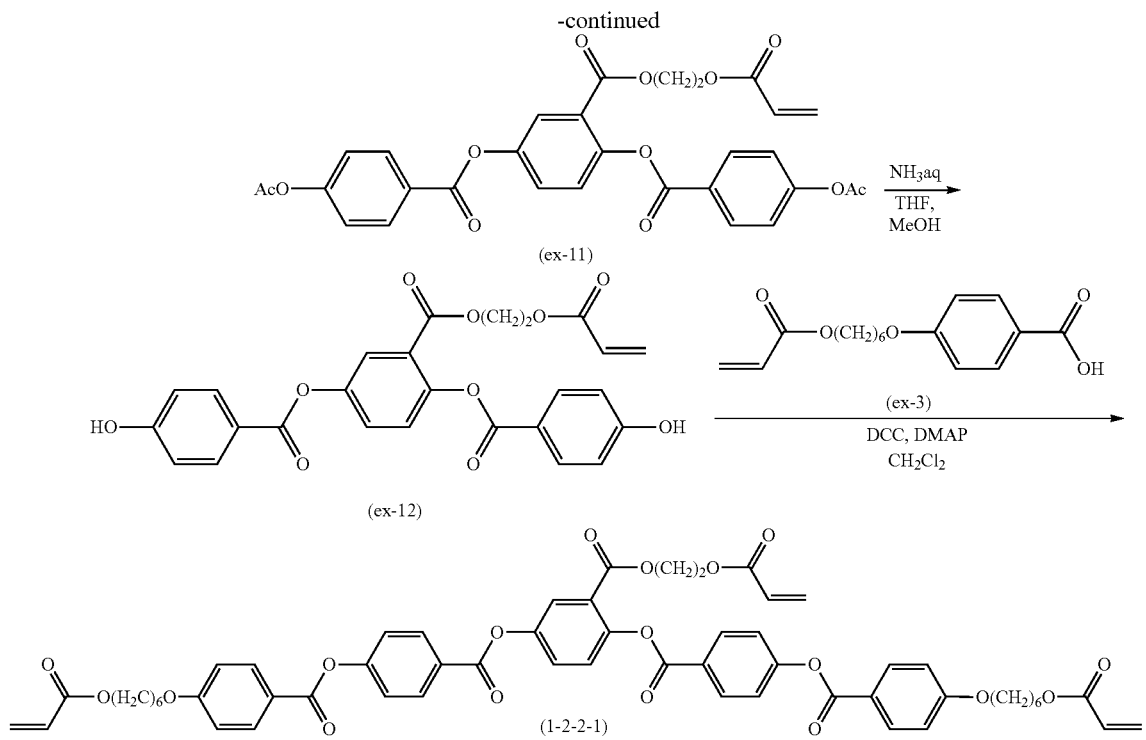

A compound ex-10 was synthesized in the same manner as in the method in European Polymer Journal 2015. 69. 584-591.

20.0 g of 4-acetoxybenzoic acid and 0.2 g of pyridine were added to 100 mL of toluene, and stirring was performed at 60° C. under a nitrogen atmosphere. 14.5 g of thionyl chloride was added dropwise thereto. After dropwise addition, stirring was performed for 4 hours at 60° C. Toluene was distilled off under a reduced pressure. The obtained residue was added to 200 mL of toluene and stirred while cooling under a nitrogen atmosphere. 100 mL of a toluene solution in which 13.7 g of the compound ex-10 and 16.8 g of triethylamine were dissolved was added dropwise thereto. After dropwise addition, stirring was performed for 4 hours at room temperature. Water was added to the stirred solution and an organic layer was extracted. Next, the organic layer was washed with water and dried with anhydrous magnesium sulfate. Toluene was distilled off under a reduced pressure, and the residue was purified through column chromatography and recrystallization was performed with a mixture (v/v=1/4) of ethyl acetate and heptane to obtain 24.4 g of a compound (ex-11). Here, the packing of the column chromatography was silica gel. Here, the eluent was a mixture (v/v=9/1) of toluene and ethyl acetate.

24.4 g of the compound ex-11 and 8 mL of a 28% by weight ammonium aqueous solution were added to a solution mixture containing 50 mL of THF and 25 mL of methanol, and stirring was performed for 4 hours at room temperature under a hydrogen atmosphere. Ethyl acetate and saturated saline were added to the reaction solution and an organic layer was extracted. Next, the organic layer was washed with saturated saline and dried with anhydrous magnesium sulfate. A solvent was distilled off under a reduced pressure and the residue was purified through column chromatography and recrystallization was performed with a mixture (v/v=1/1) of ethyl acetate and heptane to obtain 9.8 g of a compound (ex-12). Here, the packing of the column chromatography was silica gel. Here, the eluent was a mixture (v/v=2/1) of toluene and ethyl acetate.

9.8 g of the compound ex-12, 12.8 g of the compound ex-3 and 0.5 g of DMAP were added to 100 mL of dichloromethane, and stirring was performed while cooling in an ice bath at 5° C. under a nitrogen atmosphere. 18 mL of a dichloromethane solution in which 8.7 g of DCC was dissolved was added dropwise thereto. After dropwise addition, stirring was performed for 16 hours at room temperature. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 14.1 g of a compound (1-2-2-1). Here, the packing of the column chromatography was silica gel. Here, the eluent was a mixture (v/v=10/1) of toluene and ethyl acetate.

A transition temperature of the compound (1-2-2-1) from a crystal phase to a nematic phase was 68° C. A transition temperature of the compound (1-2-2-1) from a nematic phase to an isotonic liquid was 82° C.

Signals of $^1$H-NMR of the compound (1-2-2-1) were as follows.

8.31 (d, 2H), 8.28 (d, 2H), 8.17 (d, 4H), 7.96 (s, 1H), 7.51 (d, 1H), 7.40 (d, 4H), 7.33 (d, 1H), 6.99 (d, 4H), 6.44-6.35 (m, 3H), 6.17-6.02 (m, 3H), 5.86-5.79 (m, 3H), 4.43-4.40 (m, 2H), 4.25-4.21 (m, 2H), 4.19 (t, 4H), 4.08-4.03 (m, 4H), 1.89-1.82 (m, 4H), 1.77-1.70 (m, 4H), 1.59-1.44 (m, 8H).

Comparative Example 1

A structure of a compound (C-1) is shown below. The compound (C-1) was a polymerizable liquid crystal compound.

[Chem. 29]

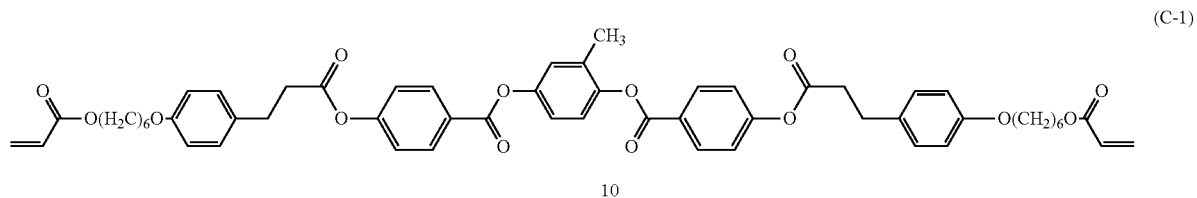

The compound (C-1) was synthesized according to the following procedure.

[Chem. 30]

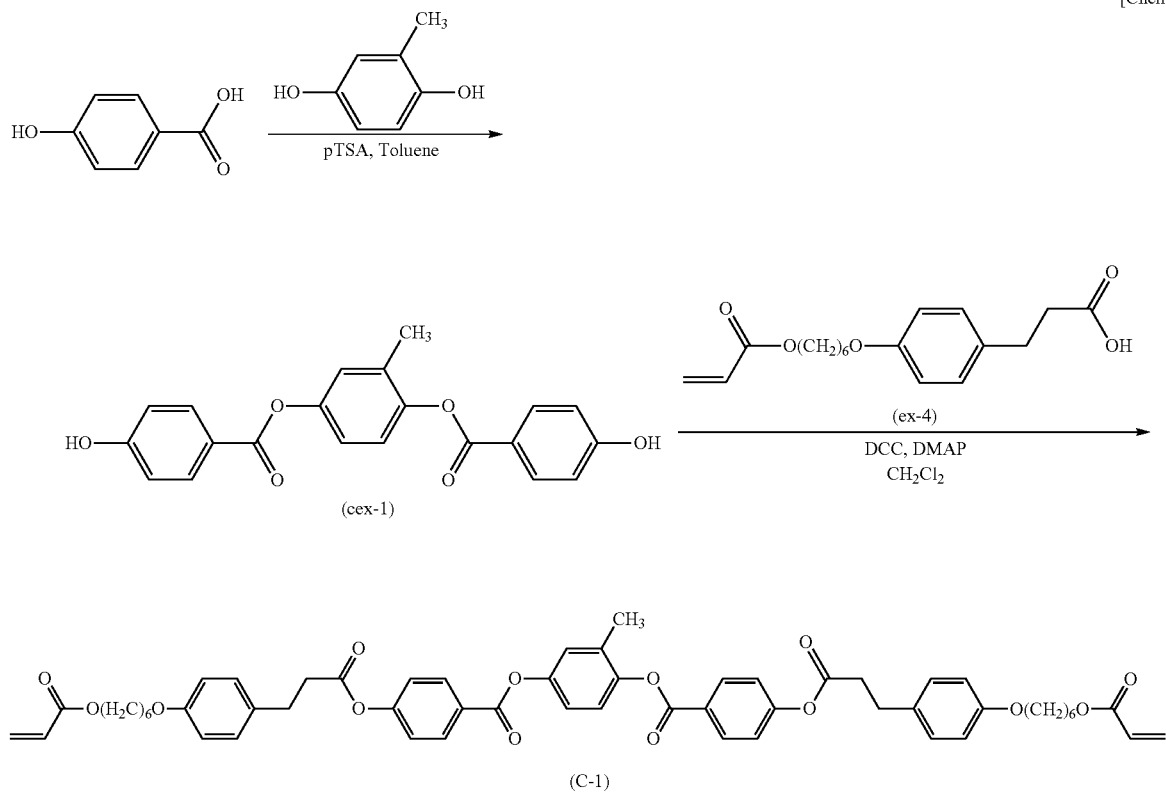

11.1 g of p-hydroxybenzoic acid, 5.0 g of methylhydroquinone and 0.5 g of pTSA were added to 100 mL of toluene, and the mixture was heated and refluxed for 8 hours while stirring and removing water in the system using a Dean-Stark apparatus under a nitrogen atmosphere. The mixture was cooled and the precipitate was separated off by filtration. The obtained crystal was washed with acetone at 50° C. to obtain 10.5 g of a compound (cex-1).

10.5 g of the compound (cex-1), 42.0 g of the compound (ex-4), and 3.2 g of DMAP were added to 400 mL of dichloromethane and stirred while cooling under a nitrogen atmosphere. 55 mL of a dichloromethane solution in which 27.5 g of DCC was dissolved was added dropwise thereto. After dropwise addition, stirring was performed for 16 hours at room temperature. The deposited precipitate was filtered and an organic layer was washed with water and dried with anhydrous magnesium sulfate. Dichloromethane was distilled off under a reduced pressure and the residue was purified through column chromatography and recrystallization was performed with methanol to obtain 35.7 g of a compound (C-1).

The packing of the column chromatography was silica gel, and the eluent was a mixture (v/v=9/1) of toluene and ethyl acetate.

Comparative Example 2

A structure of the compound (C-2) is shown below. The compound (C-2) is a polymerizable liquid crystal compound.

[Chem. 31]

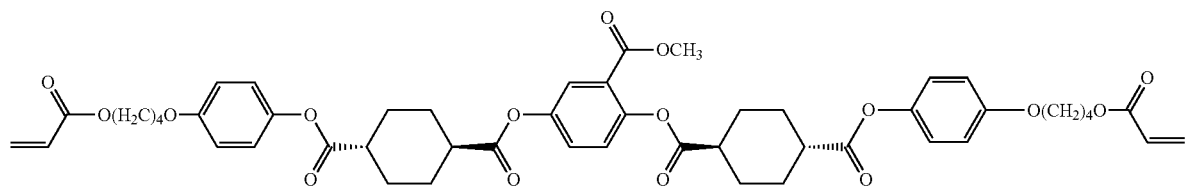
(C-2)

The compound (C-2) was synthesized according to the following procedure.

[Chem. 32]

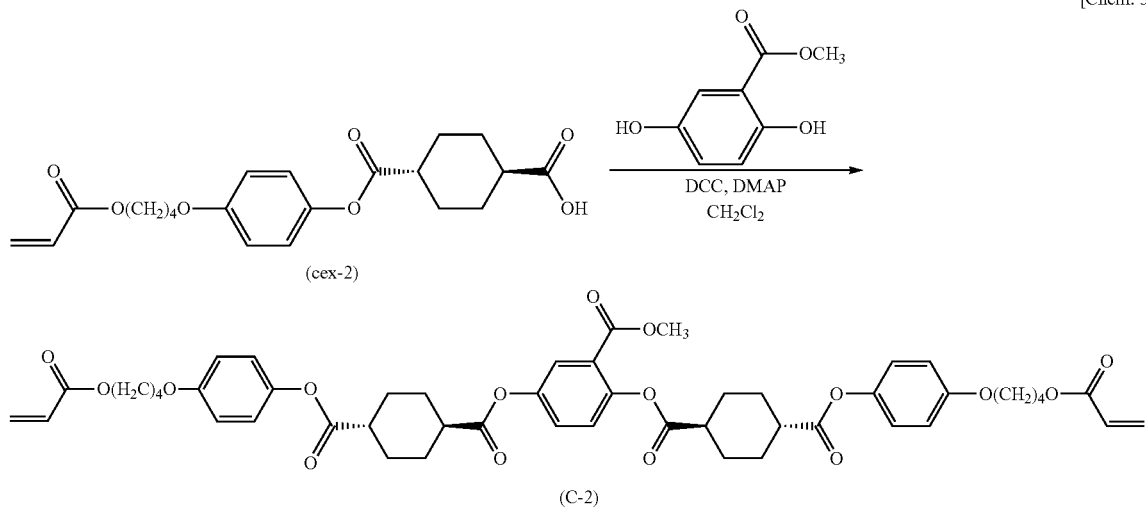

A compound (cex-2) was synthesized in the same manner as in Example 4 in Japanese Unexamined Patent Application Publication No. 2016-047813.

5.0 g of the compound (cex-2), 1.1 g of methyl 2,5-dihydroxybenzoate and 0.3 g of DMAP were added to 50 mL of dichloromethane and stirred while cooling under a nitrogen atmosphere. 5 mL of a dichloromethane solution in which 2.4 g of DCC was dissolved was added dropwise thereto. After dropwise addition, stirring was performed for 16 hours at room temperature. The deposited precipitate was filtered and an organic layer was washed with water and dried with anhydrous magnesium sulfate. Dichloromethane was distilled off under a reduced pressure and the residue was purified through column chromatography and recrystallization was performed with methanol to obtain 3.3 g of a compound (C-2).

The packing of the column chromatography was silica gel, and the eluent was a mixture (v/v=9/1) of toluene and ethyl acetate.

Comparative Example 3

A structure of a compound (C-3) is shown below. The compound (C-3) was a polymerizable liquid crystal compound.

[Chem. 33]

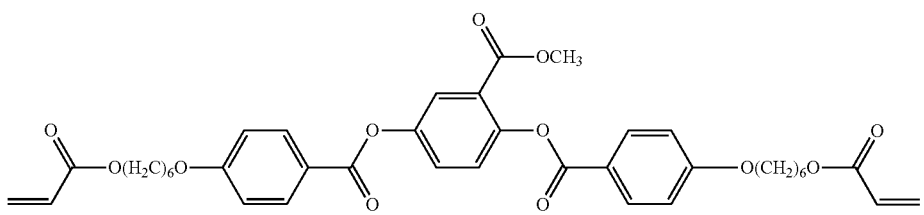
(C-3)

The compound (C-3) was synthesized in the same manner as in the method in Example 2 in Japanese Unexamined Patent Application Publication No. 2006-348022.

Comparative Example 4

A structure of a compound (C-4) is shown below. The compound (C-4) was a polymerizable liquid crystal compound.

[Chem. 34]

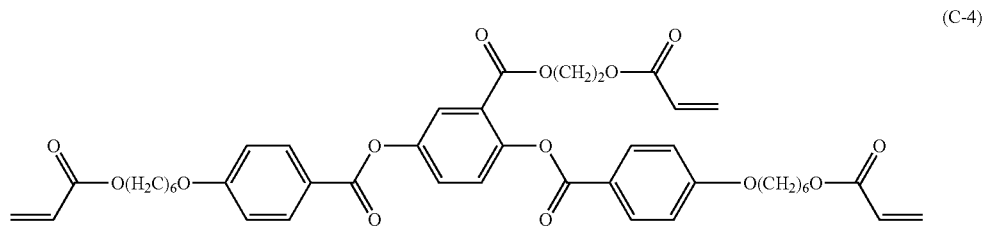

(C-4)

The compound (C-4) was synthesized in the same manner as in the method in Example 1 in Japanese Unexamined Patent Application Publication No. 2008-100982.

<Preparation of Polymerizable Liquid Crystal Composition>

A compound (M1-1-1) was synthesized in the same manner as in Japanese Unexamined Patent Application Publication No. 2003-238491 except that 2,7-dihydroxy-9-methylfluorene was used in place of 2,7-dihydroxyfluorene in the procedure of Example 3.

A compound (M2-1-1) was synthesized in the same manner as in the method in Makromolekclare Chemie (1991), 192 (1), 59-74.

[Chem. 35]

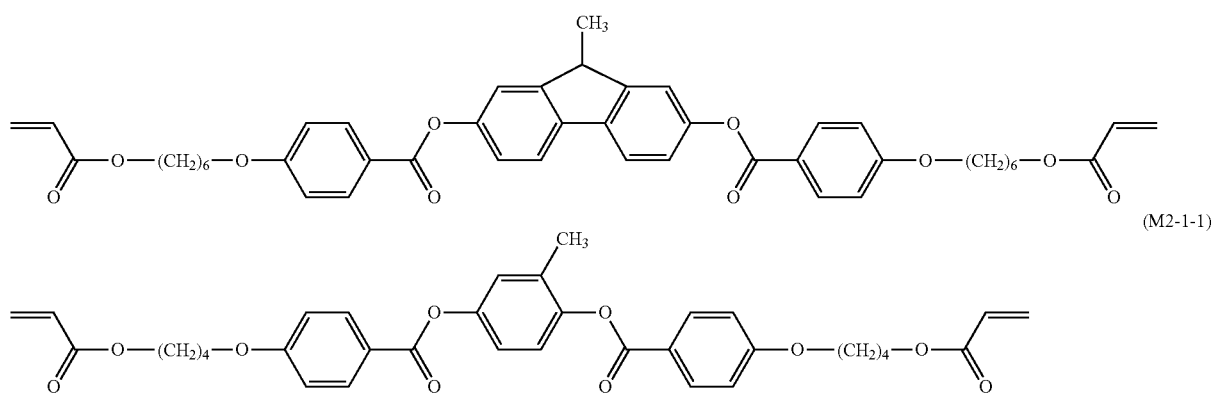

(M1-1-1)

(M2-1-1)

The compound (M1-1-1) and the compound (M2-1-1) were a polymerizable liquid crystal compound.

<Preparation of Polymerizable Liquid Crystal Composition>

<Polymerizable Liquid Crystal Composition (S-1)>

Polymerizable liquid crystal compositions (S-1) to (S-3) were prepared by mixing cyclohexanone with compounds shown in Table 1 in amounts shown in Table 1. In Table 1, 0 indicates that the corresponding compound was not mixed in.

The polymerizable liquid crystal compositions (S-1) to (S-3) contained the compound (1), and corresponded to the present invention.

TABLE 1

| Name of polymerizable liquid crystal composition | Amount and name of compound (1) | Amount of compound (M1-1-1) | Amount of compound (M2-1-1) | Amount and name of polymerization initiator | Amount and name of surfactant | Amount of cyclohexanone |
|---|---|---|---|---|---|---|
| Polymerizable liquid crystal composition (S-1) | 3.4% by weight of compound (1-1-3-1) | 11.9% by weight | 1.7% by weight | 1.02% by weight of NCI-930 | 0.05% by weight of FTX-218 | 81.93% by weight |
| Polymerizable liquid crystal composition (S-2) | 6.8% by weight of compound (1-1-3-1) | 8.5% by weight | 1.7% by weight | 1.02% by weight of Irg-907 | 0.05% by weight of TF370 | 81.93% by weight |
| Polymerizable liquid crystal composition (S-3) | 13.6% by weight of compound (1-1-1-1) | 3.4% by weight | 0 | 1.02% by weight of Irg-907 | 0.05% by weight of TF370 | 81.93% by weight |
| Polymerizable liquid crystal composition (S-4) | 13.6% by weight of compound (1-1-5-1) | 3.4% by weight | 0 | 1.02% by weight of Irg-907 | 0.05% by weight of TF370 | 81.93% by weight |
| Polymerizable liquid crystal composition (S-5) | 13.6% by weight of compound (1-1-2-1) | 3.4% by weight | 0 | 1.02% by weight of Irg-907 | 0.05% by weight of Polyflow No. 75 | 81.93% by weight |
| Polymerizable liquid crystal composition (S-6) | 6.8% by weight of compound (1-2-2-1) | 8.5% by weight | 1.7% by weight | 1.02% by weight of NCI-930 | 0.05% by weight of TF370 | 81.93% by weight |

Polymerizable liquid crystal compositions (SC-1) to (SC-3) were prepared by mixing cyclohexanone with compounds shown in Table 2 in amounts shown in Table 2. In Table 2, 0 indicates that the corresponding compound was not mixed in.

The polymerizable liquid crystal compositions (SC-1) to (SC-3) did not contain the compound (1), and did not correspond to the present invention.

TABLE 2

| Name of polymerizable liquid crystal composition | Amount and name of compound | Amount of compound (M1-1-1) | Amount of compound (M2-1-1) | Amount and name of polymerization initiator | Amount and name of surfactant | Amount of cyclohexanone |
|---|---|---|---|---|---|---|
| Polymerizable liquid crystal composition (SC-1) | 0 | 4% by weight | 16% by weight | 1.02% by weight of NCI-930 | 0.06% by weight of FTX-218 | 78.92% by weight |
| Polymerizable liquid crystal composition (SC-2) | 13.6% by weight of compound (C-1) | 3.4% by weight | 0 | 1.02% by weight of Irg-907 | 0.05% by weight of TF370 | 81.93% by weight |
| Polymerizable liquid crystal composition (SC-3) | 13.6% by weight of compound (C-2) | 3.4% by weight | 0 | 1.02% by weight of Irg-907 | 0.05% by weight of TF370 | 81.93% by weight |
| Polymerizable liquid crystal composition (SC-4) | 13.6% by weight of compound (C-3) | 3.4% by weight | 0 | 1.02% by weight of Irg-907 | 0.05% by weight of Polyflow No. 75 | 81.93% by weight |
| Polymerizable liquid crystal composition (SC-5) | 6.8% by weight of compound (C-4) | 8.5% by weight | 1.7% by weight | 1.02% by weight of NCI-930 | 0.05% by weight of TF370 | 81.93% by weight |

<Preparation of Liquid Crystal Polymerized Film with Substrate>

Example 9

A liquid crystal polymerized film with a substrate was prepared according to the following procedures.

Procedure (1) in which a polymerizable liquid crystal composition was applied onto a glass substrate with a polarized UV treated alignment film by spin coating, Procedure (2) in which the substrate was heated on a hot plate at 80° C. for 3 minutes, Procedure (3) in which the substrate was then cooled at room temperature for 3 minutes, Procedure (4) in which it was confirmed that crystals were precipitated from the polymerizable liquid crystal composition, and Procedure (5) in which light with an constant output of the ultra-high pressure mercury lamp was emitted to a polymerizable liquid crystal composition on the substrate in a direction of 90° at room temperature under a nitrogen atmosphere and the polymerizable liquid crystal composition on the substrate was polymerized.

This was provided that an optical receiver for measuring an illuminance at a wavelength of about 365 nm was used, and an emission time in the procedure (5) was adjusted to between 5 seconds and 10 seconds so that an amount of light of the ultra-high pressure mercury lamp with which a surface of the polymerizable liquid crystal composition was exposed in the procedure (5) was 500 mJ/cm$^2$.

Example 10

A liquid crystal polymerized film with a substrate was prepared for each polymerizable liquid crystal composition. Results of evaluation of the liquid crystal polymerized films with a substrate prepared using the polymerizable liquid crystal compositions are shown in Table 3. In Table 3, "—" indicates that measurement was not performed because crystals were precipitated from the polymerizable liquid crystal composition.

TABLE 3

| Name of polymerizable liquid crystal composition | Precipitation of crystals from polymerizable liquid crystal composition | Alignment of liquid crystal polymerized film | Alignment defect | Retardation | Birefringence | Front contrast |
|---|---|---|---|---|---|---|
| Polymerizable liquid crystal composition (S-1) | None | Homogeneous alignment | None | 137.8 | 0.19 | 5600 |
| Polymerizable liquid crystal composition (S-2) | None | Homogeneous alignment | None | 136.7 | 0.20 | 6400 |
| Polymerizable liquid crystal composition (S-3) | None | Homogeneous alignment | None | 140.2 | 0.21 | 7200 |
| Polymerizable liquid crystal composition (S-4) | None | Homogeneous alignment | None | 144.2 | 0.20 | 7400 |
| Polymerizable liquid crystal composition (S-5) | None | Homogeneous alignment | None | 135.5 | 0.18 | 6200 |
| Polymerizable liquid crystal composition (SC-1) | None | Homogeneous alignment | None | 139.7 | 0.17 | 4900 |
| Polymerizable liquid crystal composition (SC-2) | Present | — | — | — | — | — |
| Polymerizable liquid crystal composition (SC-3) | Present | — | — | — | — | — |
| Polymerizable liquid crystal composition (SC-4) | None | Homogeneous alignment | None | 132.1 | 0.15 | 4500 |
| Polymerizable liquid crystal composition (SC-5) | None | Homogeneous alignment | None | 133.7 | 0.13 | 3800 |

When liquid crystal polymerized films with a substrate were prepared using polymerizable liquid crystal compositions (S-1) to (S-5), no crystals were precipitated from the polymerizable liquid crystal composition. When liquid crystal polymerized films with a substrate were prepared using polymerizable liquid crystal compositions (SC-2) and (SC- 3), crystals were precipitated from the polymerizable liquid crystal composition. Therefore, a liquid crystal polymerized film with a substrate without an alignment defect were not obtained from the polymerizable liquid crystal composition (SC-2) and Compound (SC-3).

It can be understood that, when the compound (1) of the present invention is contained in a larger amount than the compounds (C-1) and (C-2), it is possible to obtain a liquid crystal polymerized film with a substrate without an alignment defect.

Front contrasts of the liquid crystal polymerized films with a substrate prepared using the polymerizable liquid crystal compositions (S-1) to (S-5) were significantly higher than front contrasts of the liquid crystal polymerized films with a substrate prepared using the polymerizable liquid crystal compositions (SC-1), (SC-4), and (SC-5).

Accordingly, it can be clearly understood that, when the polymerizable liquid crystal composition containing the polymerizable liquid crystal compound of the present invention is used as a part of a raw material, a liquid crystal polymerized film with a substrate having high front contrast is obtained.

What is claimed is:

1. A polymerizable liquid crystal composition containing a compound represented by Formula (1),

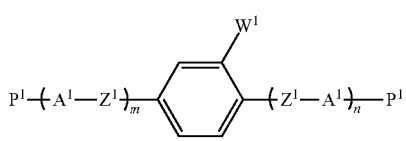

(1)

in Formula (1),
W$^1$ is an alkoxycarbonyl group having 1 to 10 carbon atoms, an alkanoyl group having 1 to 10 carbon atoms or a group represented by Formula (2), and at least one —CH$_2$— in the alkoxycarbonyl may be replaced with —O—,
A$^1$ is independently 1,4-phenylene or naphthalene-2,6-diyl, and at least one hydrogen of the 1,4-phenylene and the naphthalene-2,6-diyl may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms,
Z$^1$ is independently —CH$_2$CH$_2$—, —COO—, —OCO—, —CH$_2$O—, —OCH$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, or —COOCH$_2$CH$_2$—,
m and n are independently an integer of 0 to 7, and satisfy 3≤m+n≤8, and
P$^1$ is independently a group represented by Formula (2),

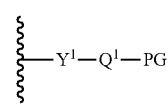

(2)

in Formula (2),
Y$^1$ is a single bond, —O—, —COO—, —OCO—, or —OCOO—,
Q$^1$ is a single bond or an alkylene group having 1 to 20 carbon atoms, and at least one —CH$_2$— in the alkylene may be replaced with —O—, —COO—, or —OCO—, and
PG is a functional group represented by any one of Formula (PG-1) to Formula (PG-9),

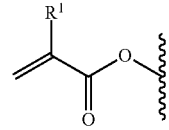

(PG-1)

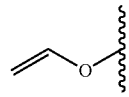

(PG-2)

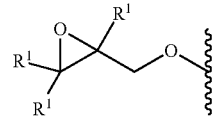

(PG-3)

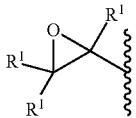

(PG-4)

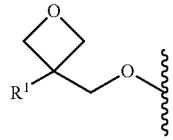

(PG-5)

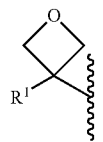

(PG-6)

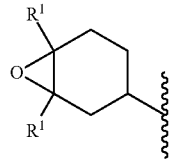

(PG-7)

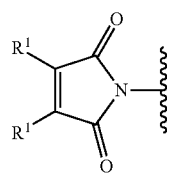

(PG-8)

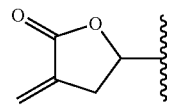

(PG-9)

in Formula (PG-1) to Formula (PG-9),
R$^1$ is independently hydrogen, halogen, methyl, ethyl, or trifluoromethyl.

2. The polymerizable liquid crystal composition according to claim 1,
wherein m and n are independently 2 or 3.

3. The polymerizable liquid crystal composition according to claim 1,
   wherein, in Formula (2), PG is a functional group represented by Formula (PG-1).

4. The polymerizable liquid crystal composition according to claim 1,
   wherein $Z^1$ is independently —COO—, —OCO—, —CH$_2$CH$_2$COO—, or —OCOCH$_2$CH$_2$—, and at least one of $Z^1$ is —CH$_2$CH$_2$COO— or —OCOCH$_2$CH$_2$—.

5. The polymerizable liquid crystal composition according to claim 1,
   wherein the compound represented by Formula (1) is contained in an amount of 1 to 50% by weight based on a total weight of the polymerizable liquid crystal composition.

6. The polymerizable liquid crystal composition according to claim 1, further containing a compound represented by Formula (M1),

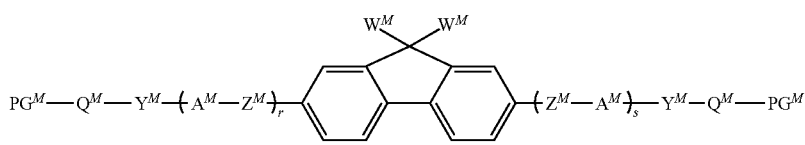

(M1)

in Formula (M1),
- $A^M$ is independently 1,4-phenylene, 1,4-cyclohexylene, or naphthalene-2,6-diyl, and at least one hydrogen in the 1,4-phenylene or the naphthalene-2,6-diyl may be replaced with fluorine, chlorine, cyano, formyl, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms,
- $Z^M$ is independently a single bond, —CH$_2$CH$_2$—, —COO—, —OCO—, —C≡C—, —CH=CHCOO—, —OCOCH=CH—, —CH$_2$CH$_2$COO—, —OCOCH$_2$CH$_2$—, —CH$_2$CH$_2$OCO— or —COOCH$_2$CH$_2$—,
- r and s are independently an integer of 1 to 3,
- $W^M$ is independently hydrogen, fluorine, chlorine, an alkyl group having 1 to 10 carbon atoms, an alkenyl group having 2 to 10 carbon atoms, or a fluoroalkyl group having 1 to 10 carbon atoms,
- $Y^M$ is independently a single bond, —O—, —COO—, —OCO—, or —OCOO—,
- $Q^M$ is independently a single bond or an alkylene group having 1 to 20 carbon atoms, and at least one —CH$_2$— in the alkylene may be replaced with —O—, —COO—, or —OCO—, and
- $PG^M$ is independently a functional group represented by any one of Formula (PG-1) to Formula (PG-9),

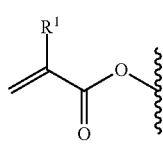
(PG-1)

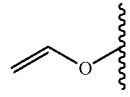
(PG-2)

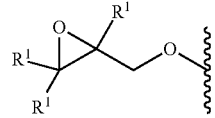
(PG-3)

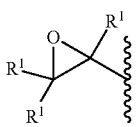
(PG-4)

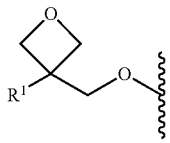
(PG-5)

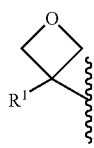
(PG-6)

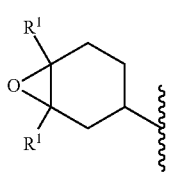
(PG-7)

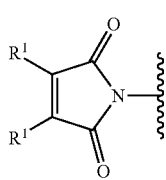
(PG-8)

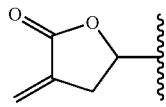
(PG-9)

in Formula (PG-1) to Formula (PG-9), $R^1$ is independently hydrogen, halogen, methyl, ethyl, or trifluoromethyl.

7. The polymerizable liquid crystal composition according to claim 6,
wherein the compound represented by Formula (1) is contained in an amount of 10 to 90% by weight based on a total weight of the compound represented by Formula (1) and the compound represented by Formula (M1).

8. The polymerizable liquid crystal composition according to claim 6,
wherein in Formula (M1), $PG^M$ is a functional group represented by Formula (PG-1).

9. A liquid crystal polymerized film obtained by polymerizing the polymerizable liquid crystal composition according to claim 1.

10. The liquid crystal polymerized film according to claim 9,
wherein liquid crystal molecules are fixed in a state where the liquid crystal molecules are aligned by the photoalignment film.

11. A retardation film composed of the liquid crystal polymerized film according to claim 9.

12. A polarizing plate having the liquid crystal polymerized film according to claim 9.

13. A display device having the liquid crystal polymerized film according to claim 9.

14. A polymerizable liquid crystal compound represented by Formula (1-1),

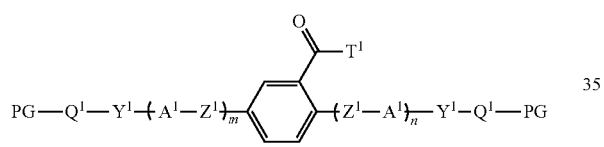

(1-1)

in Formula (1-1),
$T^1$ is an alkyl group having 1 to 10 carbon atoms or an alkoxy group having 1 to 10 carbon atoms,
$A^1$ is independently 1,4-phenylene, and at least one hydrogen in the 1,4-phenylene may be replaced with fluorine, chlorine, trifluoromethyl, an alkyl group having 1 to 5 carbon atoms, an alkoxy group having 1 to 5 carbon atoms, an alkoxycarbonyl group having 1 to 5 carbon atoms, or an alkanoyl group having 1 to 5 carbon atoms,
$Z^1$ is independently —COO—, —OCO—, —CH$_2$CH$_2$COO—, or —OCOCH$_2$CH$_2$—,
m and n each are 2 or 3,
$Y^1$ is a single bond, —O—, —COO—, —OCO—, or —OCOO—,
$Q^1$ is a single bond or an alkylene group having 1 to 20 carbon atoms, and at least one —CH$_2$— in the alkylene may be replaced with —O—, —COO—, or —OCO—, and
PG is a functional group represented by any one of Formula (PG-1) to Formula (PG-9),

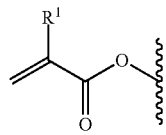

(PG-1)

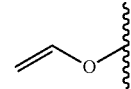

(PG-2)

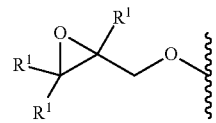

(PG-3)

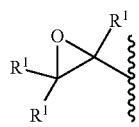

(PG-4)

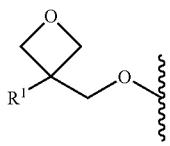

(PG-5)

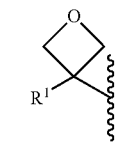

(PG-6)

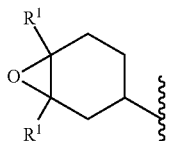

(PG-7)

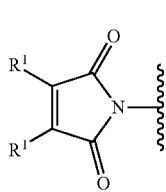

(PG-8)

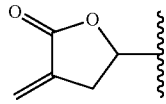

(PG-9)

in Formula (PG-1) to Formula (PG-9), $R^1$ is independently hydrogen, halogen, methyl, ethyl, or trifluoromethyl.

* * * * *